(12) United States Patent  (10) Patent No.: US 8,581,166 B2
Cho et al.  (45) Date of Patent: Nov. 12, 2013

(54) OPTOELECTRONIC SHUTTER, METHOD OF OPERATING THE SAME AND OPTICAL APPARATUS INCLUDING THE OPTOELECTRONIC SHUTTER

(75) Inventors: Yong-chul Cho, Suwon-si (KR); Jae-hyung Jang, Seoul (KR); Yong-hwa Park, Yongin-si (KR); Chang-soo Park, Daejeon (KR); Jong-in Song, Daejeon (KR)

(73) Assignees: Samsung Electronics Co., Ltd., Suwon-si (KR); Gwangju Institute of Science and Technology, Gwangju (KR)

( * ) Notice: Subject to any disclaimer, the term of this patent is extended or adjusted under 35 U.S.C. 154(b) by 800 days.

(21) Appl. No.: 12/644,744

(22) Filed: Dec. 22, 2009

(65) Prior Publication Data

US 2010/0308211 A1  Dec. 9, 2010

(30) Foreign Application Priority Data

Jun. 4, 2009 (KR) .................. 10-2009-0049475

(51) Int. Cl.
*H01L 31/0328* (2006.01)
*H01L 31/0336* (2006.01)

(52) U.S. Cl.
USPC ......... 250/208.1; 257/184; 257/187; 257/443

(58) Field of Classification Search
USPC .................................. 250/205, 214 R, 208.1
See application file for complete search history.

(56) References Cited

U.S. PATENT DOCUMENTS

| | | | |
|---|---|---|---|
| 4,935,616 A | 6/1990 | Scott | |
| 5,157,451 A | 10/1992 | Taboada et al. | |
| 5,200,793 A | 4/1993 | Ulich et al. | |
| 5,256,913 A * | 10/1993 | Sommer | 327/514 |
| 5,877,851 A | 3/1999 | Stann et al. | |
| 5,962,841 A * | 10/1999 | Okumura et al. | 250/205 |
| 6,088,086 A | 7/2000 | Muguira et al. | |
| 6,236,671 B1 | 5/2001 | Babic | |
| 6,483,094 B1 | 11/2002 | Yahav et al. | |
| 6,856,355 B1 | 2/2005 | Ray et al. | |
| 7,067,853 B1 | 6/2006 | Yao | |
| 7,361,883 B2 | 4/2008 | Xu et al. | |
| 7,391,505 B2 | 6/2008 | Dorrington | |
| 2006/0170491 A1 | 8/2006 | Wany et al. | |

FOREIGN PATENT DOCUMENTS

| | | |
|---|---|---|
| JP | 59-148033 A | 8/1984 |
| JP | 2003-279837 A | 10/2003 |
| KR | 10-2008-0038693 A | 5/2008 |
| WO | 2006/012764 A1 | 2/2006 |

OTHER PUBLICATIONS

Adrian A. Dorrington et al., "Video-rate or high-precision: A flexible range imaging camera", Image Processing: Machine Vision Applications, SPIE-IS&T, 2008, 12 pages, vol. 6813 681307.

(Continued)

*Primary Examiner* — Tony Ko
(74) *Attorney, Agent, or Firm* — Sughrue Mion, PLLC

(57) ABSTRACT

An optoelectronic shutter, a method of operating the same, and an optical apparatus including the optoelectronic shutter are provided. The optoelectronic shutter includes a phototransistor which generates an output signal from incident input light and a light emitting diode serially connected to the phototransistor. The light emitting diode outputs output light according to the output signal, and the output signal is gain-modulated according to a modulation of a current gain of the phototransistor.

24 Claims, 16 Drawing Sheets

(56) References Cited

OTHER PUBLICATIONS

Jacob Lasri et al., "HBT Optoelectronic Mixer at Microwave Frequencies: Modeling and Experimental Characterization", Journal of Lightwave Technology, Aug. 1999, 6 pages, vol. 17 No. 8.

S. W. Tan et al., "The influence of base bias on the collector photocurrent for InGaP/GaAs heterojunction phototransistors", Journal of Applied Physics, Jan. 7, 2005, 7 pages, vol. 97 No. 034502.

Weidong Zhou et al, "Low-Power Phototransceiver Arrays With Vertically Integrated Resonant-Cavity LEDs and Heterostructure Phototransistors", IEEE Photonics Technology Letters, Nov. 2001, 3 pages, vol. 13 No. 11.

Y. Betser et al., "Modeling and Performance of a One Stage InP/GaInAs Optoelectronic HBT 3-Terminal Mixer", IEEE, 1997, 4 pages.

Tsuyoshi Miyata et al., "Pulse Oximeter Using a Gain-Modulated Avalanche Photodiode Operated in a Pseudo-Lock-In Light Detection Mode", SPIE, 2006, 4 pages, vol. 6026 60260K-1.

* cited by examiner

OPTOELECTRONIC SHUTTER, METHOD OF OPERATING THE SAME AND OPTICAL APPARATUS INCLUDING THE OPTOELECTRONIC SHUTTER

CROSS-REFERENCE TO RELATED APPLICATIONS

This application claims priority from Korean Patent Application No. 10-2009-0049475, filed on Jun. 4, 2009, in the Korean Intellectual Property Office, the disclosure of which is incorporated herein in its entirety by reference.

BACKGROUND

1. Field

Apparatuses and methods consistent with the present invention relate to an optoelectronic shutter in which gain modulation is performed by using a current gain of a phototransistor, a method of operating the same, and an optical apparatus including the optoelectronic shutter.

2. Description of the Related Art

Optoelectronic shutters open and close according to an electrical waveform or pulse applied thereto. Such optoelectronic shutters may be used to modulate light that is incident on an image capture device such as a charge-coupled device (CCD) camera. For example, optoelectronic shutters may be used as a unit for obtaining information about distances between a camera and an object.

The information about the distances between the camera and the object may be obtained by using a binocular stereo vision method using two cameras or a triangulation method using structured light and a camera. However, in the binocular stereo vision method or the triangulation method, as the distances between the camera and the object increases, the accuracy of the information about the distances rapidly decreases, and the distances are dependent on the surface state of the object. Thus it is difficult to obtain accurate information about the distances.

In order to solve the problem, a time-of-flight (TOF) method has been developed. In a TOF method, a light flight time, in which modulated light is irradiated onto an object and then the light is reflected from the object and received by a light receiving unit, is measured. TOF methods include a TOF method using direct time measuring, a TOF method using correlation, and a TOF method using phase delay measuring.

In a TOF method using direct time measuring, the time in which pulse light is projected onto an object and is reflected from the object is measured.

In a TOF method using correlation, pulsed light is projected onto an object and distances between the camera and the object are measured by using information about brightness that is obtained by multiplying a gating signal that is synchronized to the projected pulsed light by a light receiving unit by a reflection light signal. In the TOF method using correlation, the amount of light of a near object that is received by the camera is large and thus the image of the object looks relatively bright, whereas the amount of light of a far object that is received by the camera is small and thus the image of the object looks relatively dark.

In a TOF method using phase delay measuring, light having a continuous wave sine wave is projected onto an object, reflected by the object, and a phase difference, that is a phase delay, of the light is detected to calculate distance. One method of phase delay measuring is that light having a frequency-modulated sine waveform that is projected onto an object and is reflected by the object is mixed at an optical modulator that is placed at a front end of a light receiving portion of the camera, and then the phase delay is measured from the mixed signal in a CCD camera. Another method of phase delay measuring is that the phase delay is measured from mixing or demodulation in a cell of the CCD camera without the optical modulator.

In addition, general optoelectronic shutters may be used as a high-speed shutter for a high-speed camera or may be used to convert or modulate incident light into data optically encoded by an optical operation system.

SUMMARY

Exemplary embodiments of the present invention overcome the above disadvantages and other disadvantages not described above. Also, the present invention is not required to overcome the disadvantages described above, and an exemplary embodiment of the present invention may not overcome any of the problems described above.

An aspect of the present invention provides an optoelectronic shutter that operates at high speed and is capable of obtaining an image of a distant object having high resolution, a method of operating the same, and an optical apparatus including the optoelectronic shutter.

Additional aspects will be set forth in part in the description which follows and, in part, will be apparent from the description, or may be learned by practice of the exemplary embodiments.

According to an aspect of the present invention, there is provided an optoelectronic shutter including a phototransistor generating an output signal from incident input light; and a light emitting diode serially connected to the phototransistor and outputting output light according to the output signal, wherein the output signal is gain-modulated according to modulation of a current gain of the phototransistor.

The light emitting diode and the phototransistor may be stacked on a substrate in a vertical direction.

The phototransistor may be a heterojunction phototransistor including a triode structure.

The light emitting diode may include a P-type cladding layer, an active layer, and an N-type cladding layer that are sequentially stacked on the substrate, and the phototransistor may include a collector layer, a base layer, and an emitter layer that are stacked sequentially on the light emitting diode.

A direct current (DC) voltage supply source, which applies a DC bias voltage, may be connected to a base of the phototransistor, and an alternating current (AC) voltage supply source, which applies an AC voltage for local oscillation of a base-emitter voltage, may be connected to an emitter of the phototransistor, and a forward voltage may be applied to the P-type cladding layer of the light emitting diode.

An emitter electrode disposed on an upper portion of the emitter layer may include a transparent conductive material, and the input light may be incident on the emitter electrode.

An anti-reflection (AR) layer may be disposed on the emitter electrode.

The optoelectronic shutter may include a structure in which a plurality of pixels, in which one of a plurality of the phototransistors and one of a plurality of the light emitting diodes constitute one of the unit pixels, are arranged. A forward voltage may be commonly applied to the P-type cladding layer of the light emitting diode of each of the plurality of pixels, a DC bias voltage may be applied to a base of the phototransistor of each of the pixels, and an AC bias voltage for local oscillation of a base-emitter voltage may be commonly applied to an emitter of the phototransistor of each of the pixels.

The light emitting diode may include an N-type cladding layer, an active layer, and a P-type cladding layer that are sequentially stacked on the substrate, and the phototransistor may include an emitter layer, a base layer, and a collector layer that are stacked sequentially on the light emitting diode.

A base current modulation unit may be connected to a base of the phototransistor.

The base current modulation unit may include: a first transistor generating a current signal that is used to modulate the base current; and a current source generating a bias current that flows through the base of the phototransistor according to the current signal generated by the first transistor.

An AC voltage for local oscillation of the base current may be applied to a base of the first transistor, and a collector of the first transistor may be connected to a collector of the phototransistor, and an emitter of the first transistor may be connected to the base of the phototransistor.

The current source may be a second transistor, and a collector and a base of the second transistor may be connected to the emitter of the first transistor, and an emitter of the second transistor may be connected to ground or a negative (−) voltage supply source.

The first and second transistors may be heterojunction bipolar transistors.

A tunnel junction layer may be interposed between the light emitting diode and the phototransistor.

A collector electrode disposed on an upper portion of the collector layer may include a transparent conductive material, and the input light may be incident on the collector electrode.

The optoelectronic shutter may include a structure in which a plurality of pixels are arranged, wherein one of a plurality of the phototransistors, one of a plurality of the first transistors, one of a plurality of the current sources, and one of a plurality of the light emitting diodes constitute one of the unit pixels.

A ground voltage or a negative (−) voltage may be commonly applied to the N-type cladding layer of the light emitting diode of each of the plurality of pixels, and a bias voltage may be commonly applied to the collector of the phototransistor of each of the pixels, and an AC bias voltage for local oscillation of a base current may be commonly applied to a base of the first transistor of each of the pixels.

A reflection layer which reflects an output light emitted from the light emitting diode, may be interposed between the light emitting diode and the phototransistor.

The reflection layer may be a distributed Bragg reflector (DBR) layer.

The substrate may include glass, sapphire, or GaAs.

The light emitting diode may be a GaP-based red light emitting diode.

The optoelectronic shutter may further include a capacitor disposed in parallel to the light emitting diode.

According to another aspect of the present invention, there is provided a method of operating an optoelectronic shutter including a phototransistor generating an output signal from incident input light; and a light emitting diode serially connected to the phototransistor and outputting output light according to the output signal, wherein the output signal is gain-modulated according to modulation of a current gain of the phototransistor, the method including modulating a base-emitter voltage of the phototransistor to modulate a current gain of the phototransistor. A DC bias voltage may be applied to a base of the phototransistor, and an AC voltage for local oscillation of the base-emitter voltage may be applied to an emitter of the phototransistor. A modulation frequency of the base-emitter voltage may be different from a modulation frequency of the input light.

According to another aspect of the present invention, there is provided a method of operating an optoelectronic shutter including a phototransistor generating an output signal from incident input light; and a light emitting diode serially connected to the phototransistor and outputting output light according to the output signal, wherein the output signal is gain-modulated according to modulation of a current gain of the phototransistor, the method including modulating a base current of the phototransistor to modulate a current gain of the phototransistor. In this case, a modulation frequency of the base current may be different from a modulation frequency of the input light.

According to another aspect of the present invention, there is provided an optical apparatus that includes the optoelectronic shutter described above.

The optical apparatus may further include: a light source irradiating light onto an object; an optical image sensor receiving the output light output from the optoelectronic shutter; and a controller controlling the light source, the optoelectronic shutter, and the optical image sensor, wherein the optoelectronic shutter gain-modulates light reflected by the object and outputs the output light, and the optical image sensor detects a phase delay of the light reflected by the object by sampling the output light.

BRIEF DESCRIPTION OF THE DRAWINGS

These and other aspects will become apparent and more readily appreciated from the following description of the exemplary embodiments, taken in conjunction with the accompanying drawings of which.

DETAILED DESCRIPTION OF EXEMPLARY EMBODIMENTS OF THE PRESENT INVENTION

Figure 1:
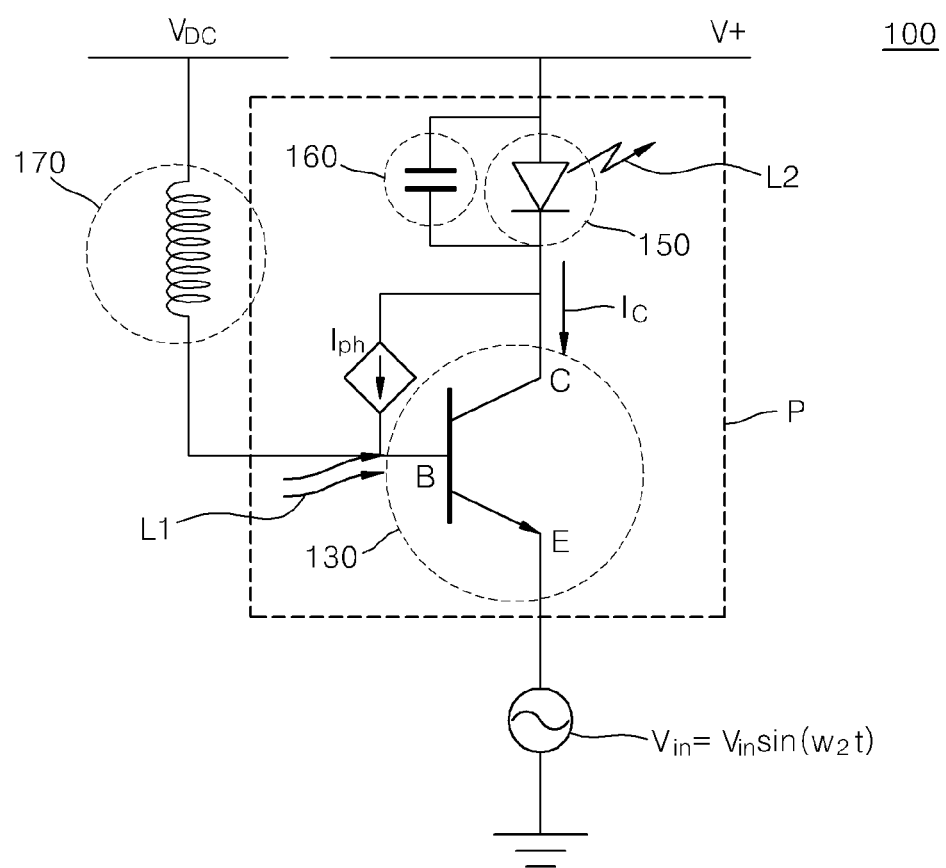
FIG. 1 is a schematic circuit diagram of an optoelectronic shutter including a unit pixel according to an exemplary embodiment.

Reference will now be made in detail to embodiments, examples of which are illustrated in the accompanying drawings, wherein like reference numerals refer to the like elements throughout. In this regard, the exemplary embodiments may have different forms and should not be construed as being limited to the descriptions set forth herein. Accordingly, the exemplary embodiments are merely described below, by referring to the figures, to explain aspects of the present description.

FIG. 1 is a schematic circuit diagram of an optoelectronic shutter 100 including a unit pixel P according to an exemplary embodiment. Referring to FIG. 1, the optoelectronic shutter 100 according to the present exemplary embodiment includes a phototransistor 130 to which an input light L1 is input and a light emitting diode 150 that outputs a gain-modulated output light L2. The optoelectronic shutter 100 may further include a capacitor 160 that controls a resistance-capacitance (RC) time constant of the light emitting diode 150. The phototransistor 130, the light emitting diode 150, and the capacitor 160 constitute the unit pixel P. The input light L1 may be infrared light having a wavelength of 800 nm, and the output light L2 may be red light having a wavelength of about 600 nm to about 700 nm.

The phototransistor 130 is an opto-electrical conversion device that is capable of amplifying current, and a heterojunction phototransistor may be used as the phototransistor 130. A case when an NPN heterojunction phototransistor is used as the phototransistor 130 will now be described. The phototransistor 130 has a triode structure in which a light current $I_{ph}$ corresponding to the input light L1 flows through a base B and is output to an emitter E. A collector C of the phototransistor 130 is serially connected to a cathode of the light emitting diode 150. An external direct current (DC) voltage supply source $V_{DC}$ is connected to the base B. An alternating current (AC) voltage supply source $V_{in}$ provided for local oscillation of an applied voltage is connected to the emitter E. An inductor 170 may be provided between the external DC voltage supply source $V_{DC}$ and the base of the phototransistor 130. The inductor 170 may be implemented as a inductance component by soldering which connects the external DC voltage supply source $V_{DC}$ to the base B of the phototransistor 130. The inductor 170 may filter high-frequency components of the DC voltage supply source $V_{DC}$.

The input light L1 is incident on the collector C of the phototransistor 130, which will be described later with reference to FIG. 3. Electron-hole pairs are formed by the input light L1 in a PN junction region formed between the base B and the collector C. Thus, the light current $I_{ph}$ corresponding to the input light L1 flows through the base B.

The light emitting diode 150 is an example of a light emitting device that outputs the output light L2 according to an output signal output from the phototransistor 130. Electrons generated in the phototransistor 130 are re-combined with holes at PN junction of the light emitting diode 150 and thus the output light L2 may be emitted. The cathode of the light emitting diode 150 is connected to the collector C of the phototransistor 130, and a voltage supply source V+, which applies a positive (+) voltage, is connected to an anode of the light emitting diode 150.

The capacitor 160 is connected in parallel to the light emitting diode 150 and controls the time constant of the light emitting diode 150.

A method of operating the optoelectronic shutter 100 will now be described with reference to FIGS. 1 and 2.

Figure 2:
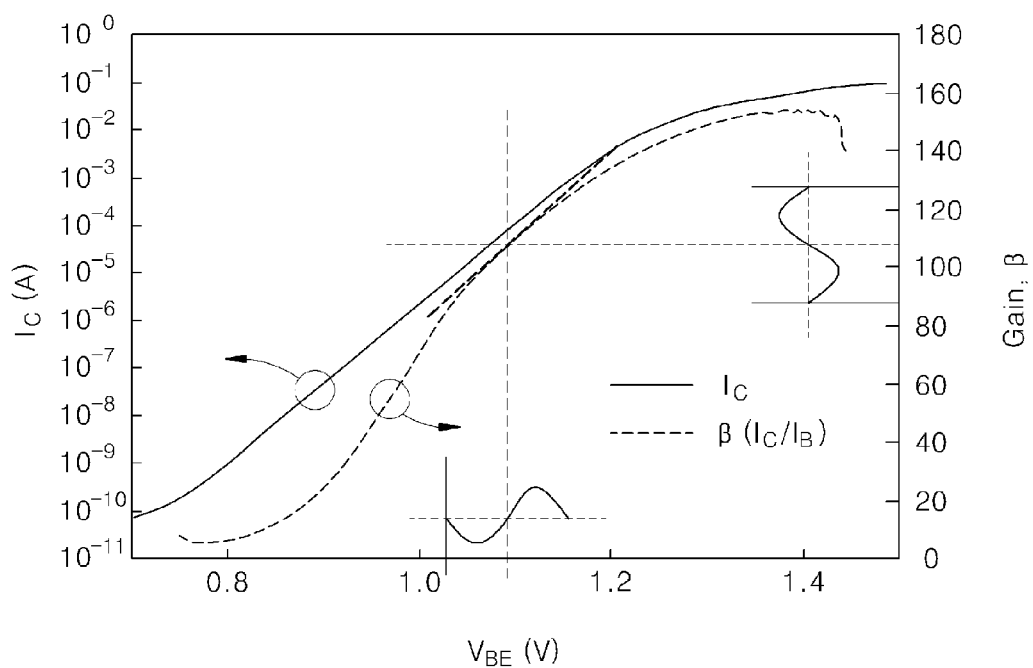
FIG. 2 is a graph showing a relationship between collector current and current gain, for varying voltages of a base-emitter voltage in the optoelectronic shutter shown in FIG. 1.

FIG. 2 is a graph of collector current $I_C$ versus current gain β, for varying voltages of a base-emitter voltage $V_{BE}$ when the concentration of beryllium (Be) used to perform P-type doping into the base B of the phototransistor 130 is $4 \times 10^{19}/cm^3$.

The base-emitter voltage $V_{BE}$ applied between the base B and the emitter E may be controlled by a method of modulating a current gain β inside the phototransistor 130 and the method may be performed in the optoelectronic shutter 100 shown in FIG. 1.

The collector current $I_C$ flows through the collector C of the phototransistor 130 and is given as an exponential function of the base-emitter $V_{BE}$. Thus, the current gain β is proportional to $\exp(V_{BE}/Vt)$ (where Vt is a thermal voltage) and varies exponentially with respect to the base-emitter voltage $V_{BE}$. Meanwhile, the collector current $I_C$ is proportional to a base current $I_B$. The current gain β is an amplification rate of the base current $I_B$ with respect to the collector current $I_C$ and is non-linear with respect to the base-emitter voltage $V_{BE}$, as shown in FIG. 2. However, when an AC voltage is applied to an operating voltage, i.e., a DC bias voltage, the collector current $I_C$ varies linearly with respect to a minor section near the operating voltage and may be obtained by using Equations 1 and 2:

$$I_C = \beta \cdot I_B = (\beta_0 + \beta_1 * V_{BE})I_B \quad (1)$$

$$V_{BE} = V_{BE0} + A_V * \sin \omega_2 t \quad (2)$$

where $V_{BE0}$ is an operating voltage applied between the base B and the emitter E, i.e., a DC bias voltage, and $A_V * \sin \omega_2 t$ is a local osillation component of voltage applied between the base B and the emitter E by the AC voltage supply source $V_{in}$.

Meanwhile, the base current $I_B$, i.e., the light current $I_{ph}$, may be obtained by using Equation 3:

$$I_B = I_{ph} = I_{ph0} + A_{ph} * \sin(\omega_1 t + \phi) \quad (3)$$

where $\omega_1$ is the frequency of the input light L1 and $\omega_2$ is the frequency of the output light L2. In other words, $\omega_1$ and $\omega_2$ are each an angular frequency, and a value that is obtained by dividing angular frequency by $2\pi$ is a general frequency; however, from hereon $\omega_1$ and $\omega_2$ are referred to as a frequency.

When the base-emitter voltage $V_{BE}$ is modulated, the frequency $\omega_2$ of the output light L2 is different from the frequency $\omega_1$ of the input light L1. The base-emitter voltage $V_{BE}$ is modulated to obtain a beat frequency $(\omega_2-\omega_1)$, which will be described later. A phase delay $\phi$ is a phase delay quantity that is proportional to a distance R between the optoelectronic shutter 100 and an object. Thus, the collector current $I_C$ may be obtained by using Equation 4:

$$I_C = I_{C01} + k \cdot \cos((\omega_2-\omega_1)t+\phi) + f(\omega_1,\omega_2,\omega_1+\omega_2) \quad (4)$$

wherein $I_{C01}$ is a DC component, and the second term of Equation 4 represents a component of a frequency difference that is obtained by mixing two frequencies $\omega_1$ and $\omega_2$. k in the second term of Equation 4 is a coefficient with respect to a cosine function. f in the third term of Equation 4 is a component including harmonic components and the sums of harmonics of the two frequencies $\omega_1$ and $\omega_2$, and may be removed by low pass filtering, wherein low pass filtering is performed by the capacitor 160. As described above, the harmonic components of the two frequencies $\omega_1$ and $\omega_2$ are removed by low pass filtering so that the gain-modulated collector current $I_C$ has a relatively low frequency that is obtained by mixing the two frequencies $\omega_1$ and $\omega_2$ and thus the optoelectronic shutter 100 shown in FIG. 1 may easily perform sampling so as to detect a phase delay, which will be described later.

The light emitting diode 150 emits according to the collector current $I_C$. The response characteristic of the light emitting diode 150 is determined by the sum of an RC time constant that includes resistance and capacitance of an active layer formed in the light emitting diode 150 and a time constant given as a carrier lifetime. In particular, the capacitance in the light emitting diode 150, which is included in the RC time constant, is proportional to the area of the active layer of the light emitting diode 150. Thus, when the light emitting diode 150 is made smaller, the capacitance in the light emitting diode 150 is reduced. When the time constant of the light emitting diode 150 is reduced, the high-frequency components of the collector current $I_C$ may not be sufficiently removed. By increasing the time constant of the light emitting diode 150, the capacitor 160, connected in parallel to the light emitting diode 150, allows the high-frequency components of the collector current $I_C$ to be filtered. When the frequency $\omega_1$ of the input light L1 is about 20 MHz to about 100 MHz, for example, the capacitance in the capacitor 160 may be set such that the beat frequency ($\omega_2-\omega_1$) may be about 30 Hz to about 60 Hz.

The optoelectronic shutter 100 shown in FIG. 1 may control the current gain $\beta$ by controlling a bias voltage when internal frequency modulation occurs, as described above, thereby functioning as a kind of electronic diaphragm. For example, the optoelectronic shutter 100 shown in FIG. 1 may increase the current gain $\beta$ when a distance between the optoelectronic shutter 100 and an object is great or a distance between the optoelectronic shutter 100 and an object is measured at low reflectivity, and may control the operating voltage so as to reduce the current gain $\beta$ when a distance between the optoelectronic shutter 100 and an object is measured at very high reflectivity.

Figure 3:
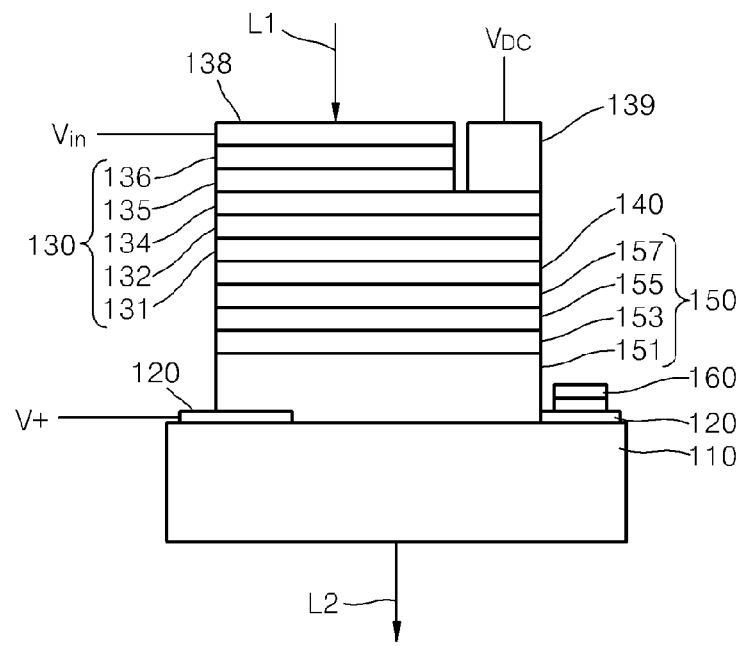
FIG. 3 is a cross-sectional view of an example of an optoelectronic shutter that may be represented by the circuit shown in FIG. 1.

FIG. 3 is a cross-sectional view of an example of the optoelectronic shutter 100 that may be represented by the circuit shown in FIG. 1. Referring to FIG. 3, the optoelectronic shutter 100 has a structure in which the light emitting diode 150 is stacked on a substrate 110 and then the phototransistor 130 is stacked on the light emitting diode 150 in a vertical direction. The input light L1 is incident on an upper portion of the phototransistor 130, and the output light L2, which is emitted from the light emitting diode 150, is emitted through the substrate 110. Furthermore, the capacitor 160 is separately provided so as to control the RC time constant of the light emitting diode 150 and is connected in parallel to the light emitting diode 150.

The light emitting diode 150 has a structure in which a P-type cladding layer 153 is formed on the substrate 110, an active layer 155 is formed on the P-type cladding layer 153, and then an N-type cladding layer 157 is formed on the active layer 155. The light emitting diode 150 may be a GaP-based red light emitting diode. Light is emitted from the active layer 155 due to re-combination of electrons transmitted by the phototransistor 130 with holes, and the active layer 155 may have a multi-quantum well (MQW) structure. For example, the active layer 155 may be an undoped InGaP/AlGaInP layer. An anode layer 151 may be disposed under the P-type cladding layer 153. The anode layer 151 may be doped to have a higher doping concentration than that of the P-type cladding layer 153 so that ohmic contact may easily be achieved.

A reflection layer 140 may be disposed on the N-type cladding layer 157. The reflection layer 140 allows upward light emitted from the active layer 155 to be reflected toward the substrate 110 disposed below the reflection layer 140 so that light may be prevented from being dispersed into the phototransistor 130 and light extraction efficiency may be increased. The reflection layer 140 may be a distributed Bragg reflector (DBR) layer in which two layers having different refractive indices and/or different thicknesses are alternately stacked. For example, the reflection layer 140 may be formed by alternately stacking an N+ type $Al_{0.3}Ga_{0.7}As$ layer and an N+ type GaAs layer.

The phototransistor 130 includes a collector layer 132, a base layer 134, and an emitter layer 135, and is disposed on the light emitting diode 150. A sub-collector layer 131 may be disposed between the reflection layer 140 and the collector layer 132. Also, a sub-emitter layer 136 may be disposed on the emitter layer 135. Due to the sub-collector layer 131 or the sub-emitter layer 136, doping concentration of the P-type cladding layer 153 increases so that ohmic contact may easily be achieved. For example, the sub-collector layer 131 may be formed of N+ type GaAs, InGaP or AlGaAs, and the collector layer 132 may be formed of N- type GaAs or InGaAs. The base layer 134 may be formed of P-type GaAs. Also, the emitter layer 135 may be formed of N-type InGaP, and the sub-emitter layer 136 may be formed of N+ type GaAs.

Part of the base layer 134 is exposed, and a base electrode 139 is disposed on the exposed part of the base layer 134. The DC voltage supply source $V_{DC}$, which applies the DC voltage, is connected to the base electrode 139. An emitter electrode 138 is disposed on the sub-emitter layer 136. The AC voltage supply source $V_{in}$ for local oscillation of an applied voltage is connected to the emitter electrode 138. The input light L1 is incident on an upper portion of the emitter electrode 138.

The base electrode 139, the emitter electrode 138, and a lower electrode 120 may be formed of a transparent conductive material such as indium tin oxide (ITO), zinc oxide (ZnO), or alumina doped zinc oxide (AZO). An anti-reflection (AR) coating layer (not illustrated) may be disposed on top surfaces of the emitter electrode 138 and the base electrode 139 so that absorption of the input light L1 may be easily performed.

The capacitor 160 may be a metal insulation metal (MIM) capacitor. The capacitor 160 may be disposed by placing the phototransistor 130 and the light emitting diode 150 and then by inserting a dielectric substance having high permittivity into the lower electrode 120.

Figure 4:
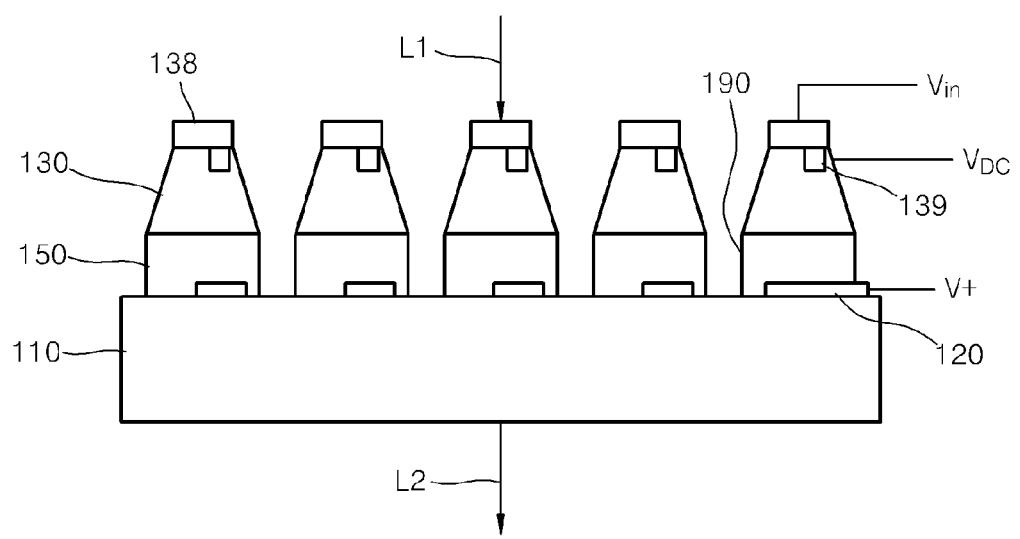
FIG. 4 is a cross-sectional view of a two-dimensional arrangement of an optoelectronic shutter that may be represented by the circuit shown in FIG. 1.
Figure 5:
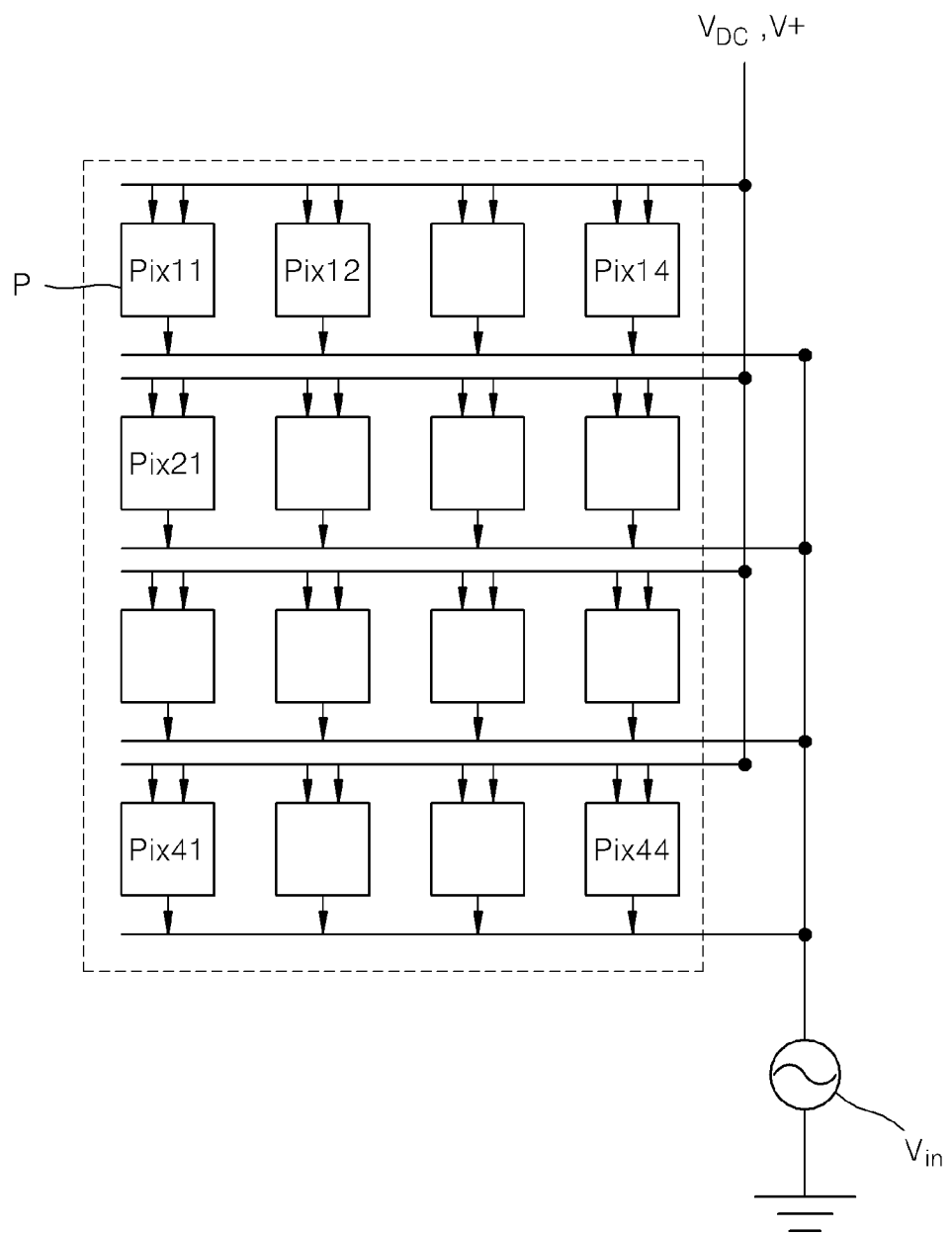
FIG. 5 is an electrical wiring diagram of the optoelectronic shutter shown in FIG. 4.

FIG. 4 is a cross-sectional view of an example of a two-dimensional (2D) arrangement of an optoelectronic shutter that may be represented by the circuit shown in FIG. 1, and FIG. 5 is an electrical wiring diagram of the optoelectronic shutter shown in FIG. 4 and illustrates a case where unit pixels are arranged in a 4×4 array.

Referring to FIGS. 4 and 5, the optoelectronic shutter according to the present exemplary embodiment has a 2D arrangement in which a plurality of the phototransistors 130 and a plurality of the light emitting diode 150 are disposed on the substrate 110 and are divided by trenches 190 into unit pixels P. Furthermore, each phototransistor 130 may be mesa etched so as to have a mesa structure. Like in the above-described exemplary embodiment, the AC voltage supply source $V_{in}$, which applies the AC voltage, and the DC voltage supply source VDC, which applies the DC voltage, are respectively connected to the emitter electrode 138 and the base electrode 139 of the phototransistor 130 of each unit pixel P, and the voltage supply source V+, which applies the positive (+) voltage, is connected to the lower electrode 120 of each unit pixel P. The lower electrode 120 may be commonly disposed on all of the unit pixels P. In this case, the AC voltage supply source $V_{in}$, which applies the AC voltage, is commonly used in each unit pixel P. Also, all of the unit pixels P may share the voltage supply source V+, which applies the positive (+) voltage, and the DC voltage supply source $V_{DC}$, which applies the DC voltage.

In the present exemplary embodiment, a case when the optoelectronic shutter has a wiring structure in which all of the two-dimensionally arranged unit pixels P of the optoelectronic shutter 100 are voltage-modulated has been described. However, for example, an independent power supply source may be provided to each unit pixel P.

The two-dimensionally arranged optoelectronic shutter is placed in front of a photographing device such as a charge-coupled device (CCD), which will be described later, and may modulate incident light. Generally, the CCD is about ⅓ inches long to about ½ inches long and the optoelectronic shutter uses an incidence and emission surface that has the same area as the CCD. If the phototransistor 130 and the light emitting diode 150 are about ⅓ inches long to about ½ inches long, then they have large time constants, and thus frequency bandwidth is reduced and frequency modulation up to several hundreds of MHz is not easily achieved. The optoelectronic shutter according to the present exemplary embodiment has a two-dimensional arrangement in which the phototransistors 130 and the light emitting diodes 150 are divided into unit pixels P and the phototransistors 130 and the light emitting diodes 150 are respectively modulated and mixed per each unit pixel P, so that high-speed frequency modulation may be performed.

Figure 6:
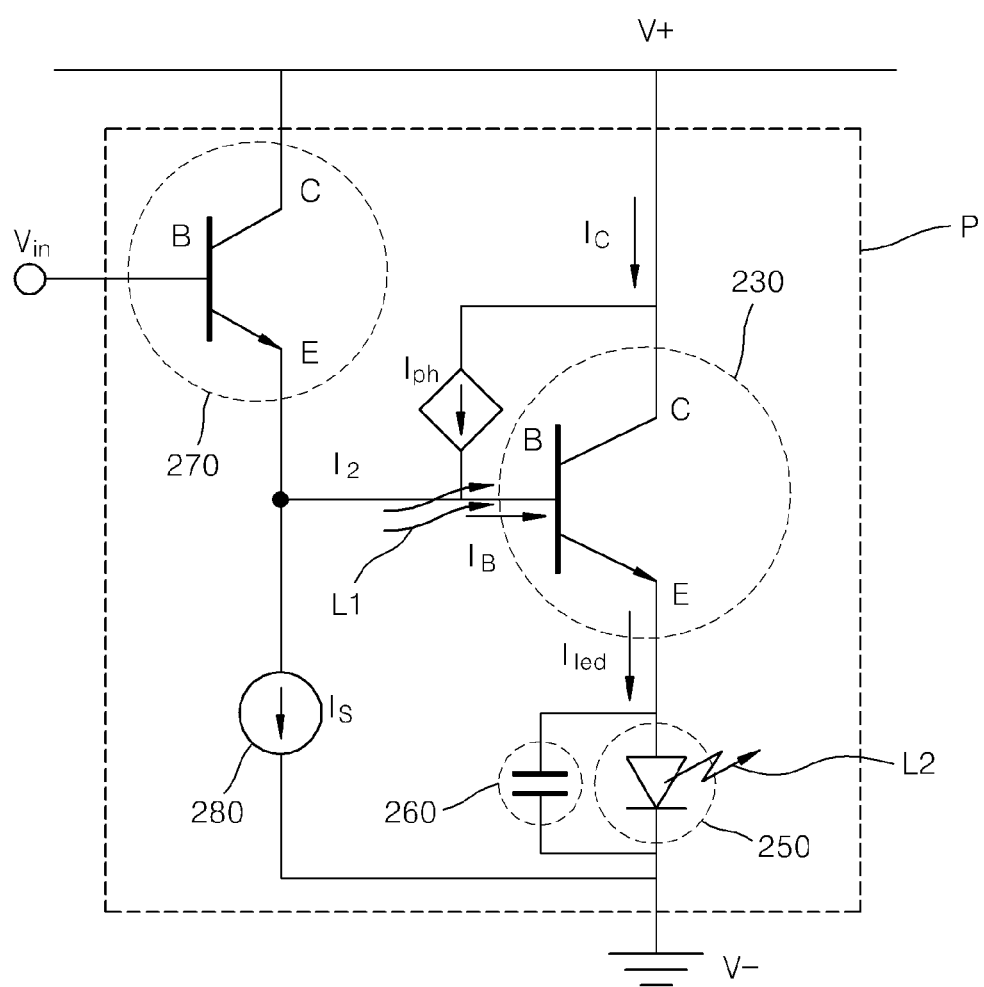
FIG. 6 is a schematic circuit diagram of an optoelectronic shutter including a unit pixel according to another exemplary embodiment.

FIG. 6 is a schematic circuit diagram of an optoelectronic shutter 200 including a unit pixel P according to another exemplary embodiment. Referring to FIG. 6, the optoelectronic shutter 200 according to the present exemplary embodiment includes a phototransistor 230 to which an input light L1 is input, a light emitting diode 250, a first transistor 270, and a current source 280. The optoelectronic shutter 200 may further include a capacitor 260 that controls an RC time constant of the light emitting diode 250. The phototransistor 230, the light emitting diode 250, the capacitor 260, the first transistor 270, and the current source 280 constitute the unit pixel P.

The phototransistor 230 performs photoelectric conversion and light signal amplification. A heterojunction transistor having a triode structure in which a light current $I_{ph}$ corresponding to the input light L1 flows through a base B and is output to an emitter E may be used as the phototransistor 230. A case in which an NPN heterojunction phototransistor is used as the phototransistor 230 will now be described. A collector C of the phototransistor 230 is placed in an upper portion of the optoelectronic shutter 200, which will be described later, and the input light L1 is incident on the collector C of the phototransistor 230. The collector C of the phototransistor 230 is connected to a voltage supply source V+, and the emitter E is serially connected to the light emitting diode 250. A current $I_2$ modulated by a voltage supply source 280 flows through the base B of the phototransistor 230 together with the light current $I_{ph}$ of the input light L1.

The light emitting diode 250 is an example of a light emitting device that outputs an output light L2 according to an output signal output from the phototransistor 230. An anode of the light emitting diode 250 is connected to the emitter E of the phototransistor 230, and a cathode of the light emitting diode 250 is grounded or is connected to a voltage supply source V−, which applies a negative (−) voltage.

The first transistor 270 and the current source 280 are an example of a base current modulation unit that modulates a base current $I_B$ that flows through the base B of the phototransistor 230. The first transistor 270 may be a heterojunction bipolar transistor, for example. The collector C of the first collector 270 is connected to the voltage supply source V+, and the emitter E is connected to the current source 280 and the base B of the phototransistor 230. An AC voltage supply source $V_{in}$ is connected to a base B of the first transistor 270. The first transistor 270 generates a current signal that is modulated by the AC voltage supply source $V_{in}$.

The current source 280 is a device that generates a bias current from the current signal generated by the first transistor 270 and may be manufactured by using a second transistor (281 of FIG. 8), which will be described later.

The capacitor 260 is connected in parallel to the light emitting diode 250 and controls a time constant of the light emitting diode 250.

A method of operating the optoelectronic shutter 200 will now be described with reference to FIGS. 6 and 7.

A method of controlling the base current $I_B$ is a method of modulating a current gain β inside the phototransistor 230 and is performed in the optoelectronic shutter 200 shown in FIG. 6.

Figure 7:
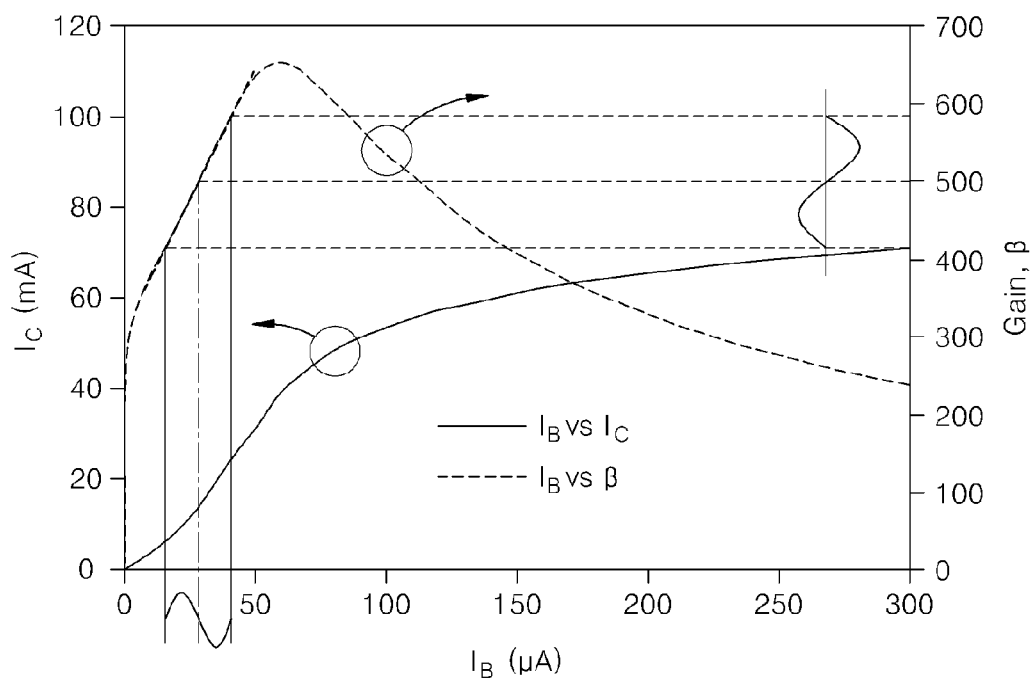
FIG. 7 is a graph showing a relationship between collector current and current gain, for varying currents of a base current in the optoelectronic shutter shown in FIG. 6.

FIG. 7 is a graph of collector current $I_C$ versus current gain β, for varying currents of a base current $I_B$ of the phototransistor 230 when the concentration of beryllium (Be) used to perform P-type doping into the base B of the phototransistor 230 is $4 \times 10^{18}/cm^3$. A section in which the current gain β, comparatively, linearly increases with respect to the base current $I_B$ is present in FIG. 7. The optoelectronic shutter 200 according to the present exemplary embodiment applies the base current $I_B$ as a bias current corresponding to the section in which the current gain β comparatively linearly increases with respect to the base current $I_B$ to the base B of the phototransistor 230. When the bias current is applied to the base B of the phototransistor 230 and the base current $I_B$ is modulated near an operating point, the current gain β is modulated and frequency mixing with the input light L1 may not be achieved.

The current gain β inside the phototransistor 230 may vary according to the doping concentration of the base B. When the doping concentration of the base B of the phototransistor 230 is $4 \times 10^{18}/cm^3$, the optical characteristic of the phototransistor 230 is improved, and a high current gain β of 500 may be obtained. Meanwhile, when the doping concentration of the base B of the phototransistor 230 is increased by $4 \times 10^{19}/cm^3$, the electrical characteristic of the phototransistor 230 is improved, but the current gain β inside the phototransistor 230, which indicates the optical characteristic of the phototransistor 230, is slightly non-linear with respect to the base current $I_B$, and an increment in the current gain β according to the variation of the base current $I_B$ is reduced.

In FIG. 7, the current gain β varies linearly in a region in which the base current $I_B$ is equal to or less than 60 μA, and the current gain β is rapidly reduced in a region in which the base current $I_B$ is equal to or greater than 60 μA. This is because when the base current $I_B$ is increased to a given value, the base current $I_B$ is in a high level injection region, a relationship between a minority carrier and a junction voltage is not represented by an exponential function in a base-emitter junction and a base-collector junction, and thus the current gain β is rapidly reduced.

The relationship between the base current $I_B$ and the current gain β in a linear section may be obtained by using Equations 5 and 6:

$$\beta = \beta_0 + \beta_1 \cdot I_B \quad (5)$$

$$I_C = \beta \cdot I_B = (\beta_0 + \beta_1 \cdot I_B) I_B \quad (6)$$

When the bias current that flows through the base B of the phototransistor 230 due to a gate voltage applied to the first transistor 270 is $I_2$, the current $I_B$ flowing through the base B of the phototransistor 230 may be obtained by using Equation 7:

$$I_B = I_{ph} + I_2 \quad (7)$$

In the present exemplary embodiment, the light current $I_{ph}$ generated due to the input light L1 may be about 10 nA to about 100 nA. In this case, a current source is designed to apply a current $I_2$ of several tens of μA, thereby setting $I_{ph} \ll I_2$. Equation 7 may be expressed under the above setting condition, as shown in Equation 8:

$$I_C = \beta_0 (I_{ph} + I_2) + \beta_1 (I_{ph} + I_2)^2 \approx \beta_0 \cdot I_2 + 2\beta_1 \cdot I_{ph} \cdot I_2 + \beta_1 \cdot I_2^2 \quad (8)$$

where $I_2 = I_{20} + A_i^* \sin \omega_2 t$, and $I_{ph} = I_{ph0} + A_{ph}^* \sin(\omega_1 t + \Phi)$.

Also, Equation 7 may be again expressed, as shown in Equation 9:

$$I_C = I_{C02} + k_1^* \cos((\omega_2 - \omega_1)t + \Phi) + f(\omega_1, \omega_2, \omega_1 + \omega_2) \quad (9)$$

Equation 9 has a similar form to that of Equation 4. The collector current $I_C$, which is used to drive the light emitting diode 250, is given by a DC component $I_{C02}$, a component of a frequency difference that is obtained by mixing two frequencies $\omega_1$ and $\omega_2$, and a high-frequency component function f. $k_1$ in the second term of Equation 9 is a coefficient with respect to a cosine function. The high-frequency component function f in the third term of Equation 9 is given as a function of the frequencies $\omega_1$, $\omega_2$, and the sum ($\omega_1 + \omega_2$) (where $\omega_1 + \omega_2$ are modulated frequencies). The high-frequency component function f is filtered by the capacitor 260 connected in parallel to the light emitting diode 250.

Figure 8:
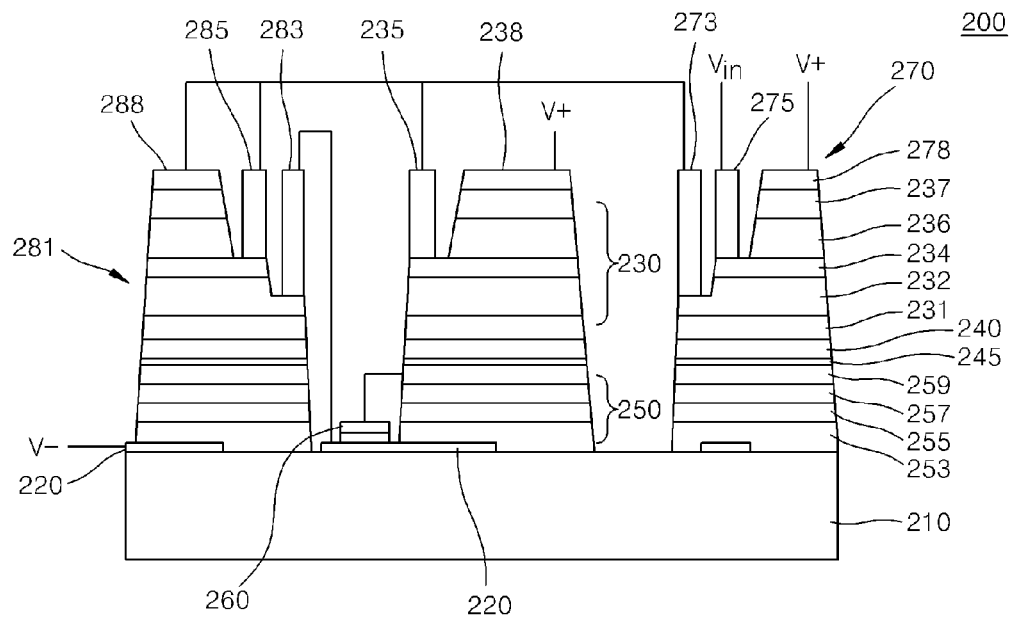
FIG. 8 is a cross-sectional view of an example of an optoelectronic shutter that may be represented by the circuit shown in FIG. 6.

FIG. 8 is a cross-sectional view of an example of the optoelectronic shutter 200 that may be represented by the circuit shown in FIG. 6. Referring to FIG. 8, the optoelectronic shutter 200 according to the present exemplary embodiment includes the phototransistor 230, the light emitting diode 250, the first transistor 270, and the second transistor 281. Furthermore, the capacitor 260 is separately provided so as to control the RC time constant of the light emitting diode 250 and is connected in parallel to the light emitting diode 250.

A substrate 210 may be formed of a material that is transparent with respect to the output light L2 emitted from the light emitting diode 230. For example, the substrate 210 may be formed of glass, sapphire, or GaAs having a thickness of about 200 μm to about 500 μm.

In the present exemplary embodiment, the optoelectronic shutter 200 has a structure in which the phototransistor 230 is disposed on the light emitting diode 250 and the light emitting diode 250 is disposed on the substrate 210. Furthermore, the light emitting diode 250 with phototransistor 230, the first transistor 270, and the second transistor 281 may be formed of the same stack structure. In FIG. 8, reference numerals of layers of the first transistor 270 also apply to those of layers of the light emitting diode 250 with phototransistor 230 and the second transistor 281. A trench or a mesa trench is formed between the light emitting diode 250 or phototransistor 230, the first transistor 270, and the second transistor 281 so that the light emitting diode 250 with phototransistor 230, the first transistor 270, and the second transistor 281 may be electrically separated from one another.

The light emitting diode 250 includes an N-type cladding layer 255, an active layer 257, and a P-type cladding layer 259, wherein the light emitting diode 250 is disposed on the substrate 210. An N-type cathode layer 253 may be further disposed under the N-type cladding layer 255 doped with an N-type dopant. The light emitting diode 250 may be a GaP-based red light emitting diode. A lower electrode 220 is disposed between the substrate 210 and the N-type cathode layer 253. The capacitor 260 is connected to both the P-type cladding layer 259 of the light emitting diode 250 and the lower electrode 220.

The phototransistor 230 and the light emitting diode 250 are PN-joined to each other. Thus, in order to reduce resistance in a PN-junction, a tunnel junction layer 245 may be interposed between the phototransistor 230 and the light emitting diode 250. The tunnel junction layer 245 may be formed as a double layer in which a highly-doped P++ type GaAs layer and a highly-doped N++ type GaAs layer are PN-joined to each other, having a thickness of several tens of nm.

A reflection layer 240 may be interposed between the tunnel junction layer 245 and the phototransistor 230, wherein the reflection layer 240 reflects light emitted from the light emitting diode 250 toward a lower portion of the substrate 210. The reflection layer 240 reflects light emitted upward from the active layer 255 toward the substrate 210. The reflection layer 240 may be a DBR layer in which an N+ type $Al_{0.3}Ga_{0.7}As$ layer and an N+ type GaAs layer are alternately stacked.

The phototransistor 230 includes an emitter layer 232, a base layer 234, and a collector layer 236, and is disposed on the light emitting diode 250. A collector layer 236 is disposed on an upper portion of the phototransistor 230, and the input light L1 is incident on the collector layer 236. A collector electrode 238 is disposed in an upper portion of the collector layer 236 of the phototransistor 230, and part of the base layer 234 is exposed so that a base electrode 235 may be formed. A highly-doped sub-emitter layer 231 may be interposed between the emitter layer 232 and the reflection layer 240, and a highly-doped sub-collector layer 237 may be interposed between the collector layer 236 and the collector electrode 238. For example, the sub-emitter layer 231 may be formed of N+ type GaAs, and the emitter layer 232 may be formed of N-type InGaP. The base layer 234 may be formed of P-type GaAs. Also, the collector layer 236 may be formed of N– type GaAs or InGaAs, and the sub-collector layer 237 may be formed of N+ type GaAs, InGaP, or AlGaAs. The collector electrode 238, the base electrode 235, and the lower electrode 220 may be formed of a transparent conductive material such as ITO, ZnO, or AZO.

The first transistor 270 and the second transistor 281 are stacked on the substrate 210 in the same manner as that of the phototransistor 230. For electrical wiring that will be described later, the first transistor 270 and the second transistor 281 respectively include base electrodes 275 and 285 and collector electrodes 278 and 288, and part of the emitter layer 232 is exposed so that emitter electrodes 273 and 283 may be formed.

The first transistor 270 is used in current modulation, and the second transistor 281 is used as a current source. A mesa trench may be formed between the phototransistor 230, the first transistor 270, and the second transistor 281 so that the phototransistor 230, the first transistor 270, and the second transistor 281 may be electrically insulated from one another. The sizes of the phototransistor 230, the first transistor 270, and the second transistor 281 shown in FIG. 8 are not based on their actual sizes. For example, the phototransistor 230 may be formed to be equal to or larger than 90% of a pixel area, and the first transistor 270 and the second transistor 281 may be formed to be equal to or less than 10% of the pixel area.

Electrical connection between respective elements will now be described.

The collector electrode 238 of the phototransistor 230 and the collector electrode 278 of the first transistor 270 are connected to the voltage supply source V+, which applies a positive (+) voltage. The base electrode 275 of the first transistor 270 is connected to the AC voltage supply source $V_{in}$ controlling the gate voltage applied to the first transistor 270, and the emitter electrode 273 of the first transistor 270 is connected to the base electrode 235 of the phototransistor 230. In addition, the emitter electrode 273 of the first transistor 270 is connected to a voltage supply source V−, which applies a negative (−) voltage via the second transistor 281, which is a current source.

The base electrode 285 and the collector electrode 288 of the second transistor 281 are connected to each other and are also connected to the emitter electrode 273 of the first transistor 270. The emitter electrode 283 of the second transistor 281 is connected to the voltage supply source V−. The second transistor 281 having the above wiring structure functions as a current source that generates a bias current from the current signal generated by the first transistor 270. The second transistor 281 may be a current source. However, for example, various current sources may be used in the present exemplary embodiment.

The N-type cathode layer 253 of the light emitting diode 250 and the emitter electrode 283 of the second transistor 281 are connected to the lower electrode 220, and the lower electrode 220 is connected to the voltage supply source V−, which applies the negative (−) voltage. The lower electrode 220 may be grounded instead of being connected to the voltage supply source V−.

The capacitor 260 is connected in parallel to the light emitting diode 250. In other words, ends of the capacitor 260 are respectively connected to the P-type cladding layer 259 of the light emitting diode 250 and the lower electrode 220.

Figure 9:
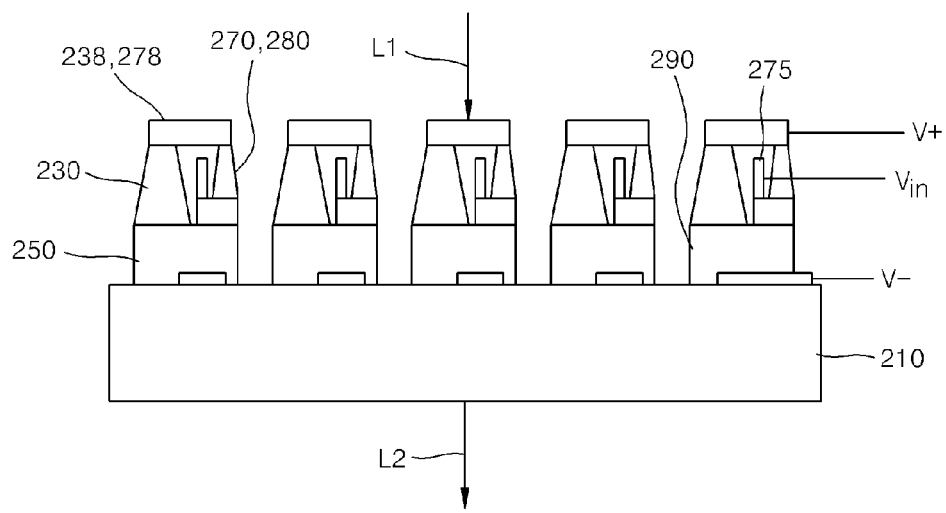
FIG. 9 is a cross-sectional view of a two-dimensional arrangement of an optoelectronic shutter that may be represented by the circuit shown in FIG. 6.
Figure 10:
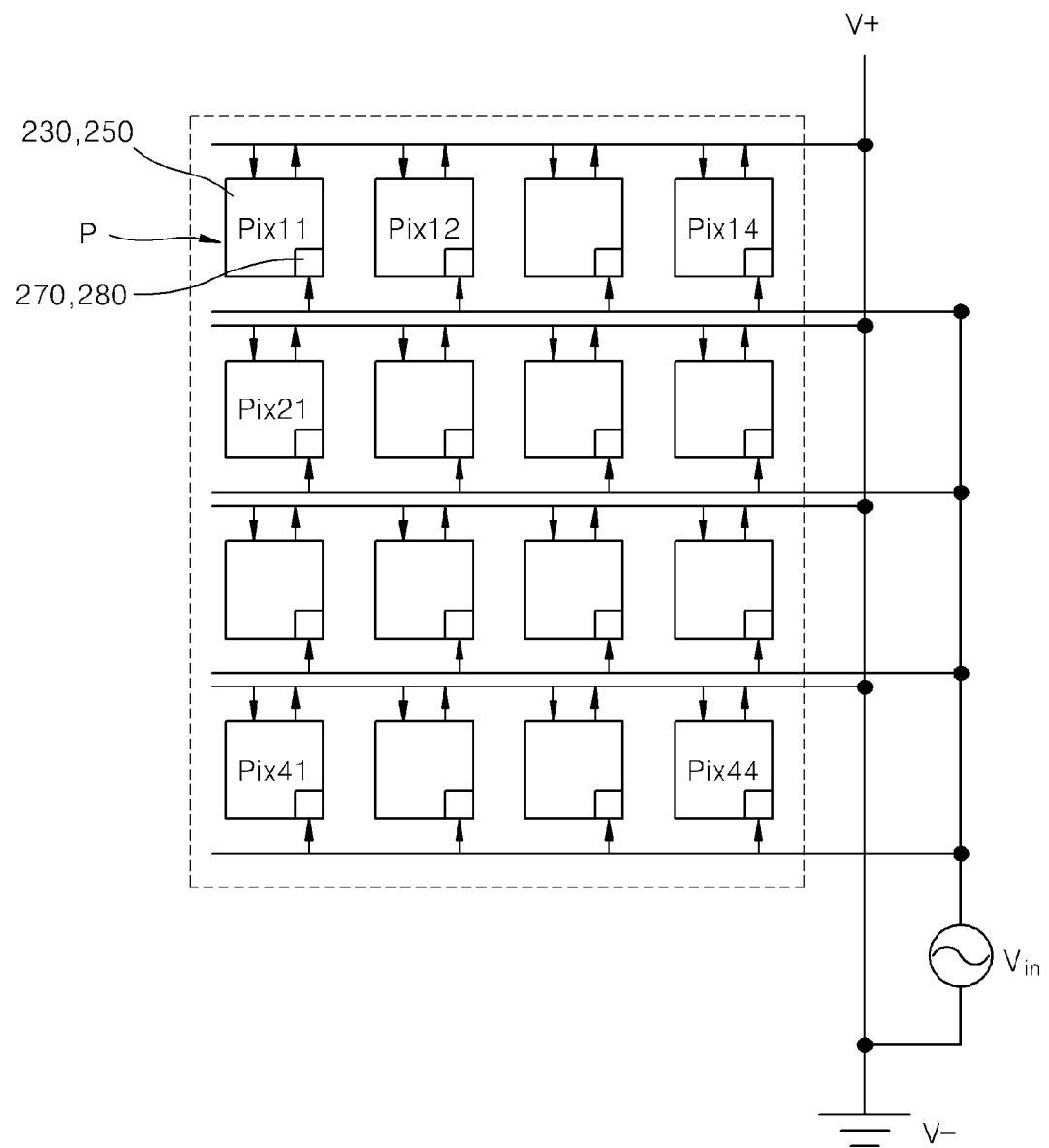
FIG. 10 is an electrical wiring diagram of the optoelectronic shutter shown in FIG. 9.

FIG. 9 is a cross-sectional view of a 2D arrangement of an optoelectronic shutter that may be represented by the circuit shown in FIG. 6, and FIG. 10 is an electrical wiring diagram of the optoelectronic shutter shown in FIG. 9 and illustrates the case where unit pixels are arranged in a 4×4 array.

Referring to FIGS. 9 and 10, the optoelectronic shutter according to the present exemplary embodiment has a 2D arrangement in which a plurality of the phototransistors 230, a plurality of the light emitting diodes 250, a plurality of the first transistors 270, and a plurality of the current sources 280, which are disposed on the substrate 210, are divided by trenches 290 into unit pixels P. Furthermore, each phototransistor 230, each first transistor 270, and each current source 280 may be mesa etched so as to have a mesa structure. Like in the above-described exemplary embodiment as described with reference to FIGS. 6 through 8, the collector electrode 238 of the phototransistor 230 and the collector electrode 278 of the first transistor 270 of each unit pixel P are connected to the voltage supply source V+, which applies the positive (+) voltage. The base electrode 275 of the first transistor 270 of each unit pixel P is connected to the AC voltage supply source $V_{in}$, and the current source 280 and the lower electrode 220 of each unit pixel P are connected to the voltage supply source V−, which applies a ground voltage or the negative (−) voltage. The lower electrode 220 may be disposed commonly to all of the unit pixels P. In this case, the voltage supply source V−, which applies a ground voltage or the negative (−) voltage, is commonly used in each unit pixel P. Also, all of the unit pixels P may share the voltage supply source V+, which applies the positive (+) voltage, and the AC voltage supply source $V_{in}$.

In the present exemplary embodiment, a case in which the optoelectronic shutter has a wiring structure in which all of the two-dimensionally arranged unit pixels P of the optoelectronic shutter are voltage-modulated has been described. However, for example, an independent power supply source may be provided to each unit pixel P.

Figure 11:
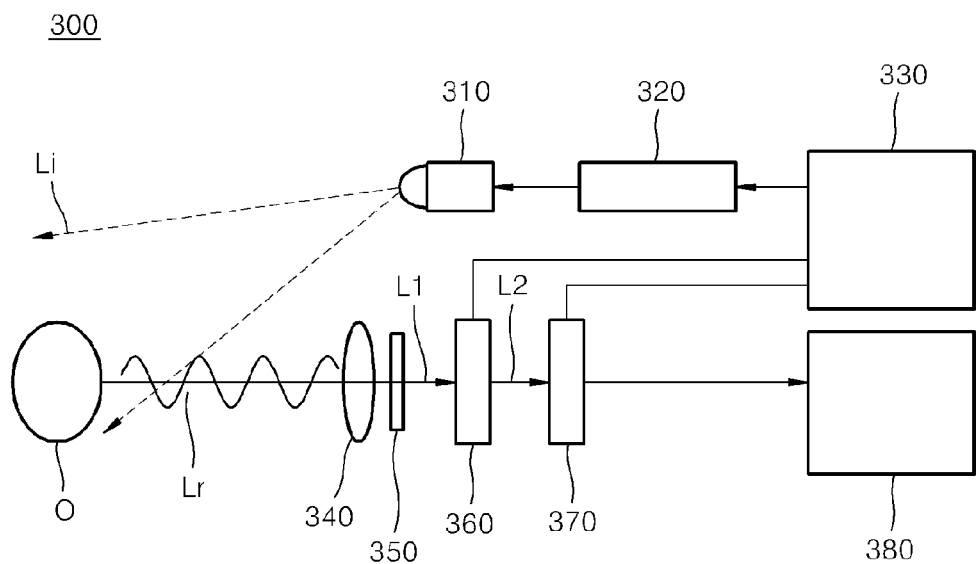
FIG. 11 illustrates an optical apparatus including an optoelectronic shutter according to an exemplary embodiment.

FIG. 11 illustrates an optical apparatus 300 including an optoelectronic shutter according to an exemplary embodiment. Referring to FIG. 11, the optical apparatus 300 is camera that includes a light source 310 that emits an irradiation light Li, a light source driver 320, a camera controller 330, an optoelectronic shutter 360, and an optical image sensor 370. The optical apparatus 300 further includes a lens 340 that focuses a reflected light Lr reflected by an object O, and a filter 350 that filters the focused irradiation light Lr. The lens 340, the filter 350, the optoelectronic shutter 360, and the optical image sensor 370 may be arranged in a line on the same optical axis. Reference numeral 380 denotes a computer to which a 3D image including distance information output from the optical image sensor 370 is input.

The irradiation light Li emitted from the light source 310 may be infrared light having a sine waveform or a pulse waveform.

The light source driver 320 drives and controls the light source 310 at a frequency $\omega_1$. The camera controller 330 controls operation of the light source driver 320, the optoelectronic shutter 360, and the optical image sensor 370.

The optical image sensor 370 may be a CCD or a complementary metal oxide semiconductor (CMOS), for example. The lens 340 collects the reflected light Lr reflected by the object O to be incident on the filter 350. The filter 350 is a pass filter that removes noise light and passes the irradiation light Li from the reflected light Lr and may be an infrared (IR) pass filter.

The optoelectronic shutter 360 may be any one of the optoelectronic shutters 100 and 200 shown in FIGS. 1 and 6. The optoelectronic shutter 360 modulates a current gain of a signal output from the input light L1 to have a frequency $\omega_2$, thereby generating the output light L2 having a lowered frequency.

The output light L2 generated by the optoelectronic shutter 360 is sampled by the optical image sensor 370 and thus phase delay between the irradiation light Li and the reflection light Lr may be obtained. Since phase delay is given as a function of distance, the optical image sensor 370 obtains distance information according to each unit pixel P so that a 3D image may be realized. The optical image sensor 370 according to the present exemplary embodiment samples the output light L2 having a lowered frequency by the optoelectronic shutter 360. Thus, additional devices and additional circuits that perform high-speed switching are not used, and a CCD image sensor or a CMOS image sensor as a general 2D image sensor may be used so that an image of a distant object having high resolution may be easily obtained.

A general camera producing 3D images uses a method of modulating and demodulating light inside the CCD image sensor. Thus, a signal processing circuit is disposed around a unit pixel within a unit device such that the size of the unit pixel increases and the general camera may not be manufactured to have high resolution. On the other hand, only a general CCD image sensor or a general CMOS image sensor may be used in a camera using the optoelectronic shutter 360 according to the present exemplary embodiment, and thus high resolution may be easily achieved by using the camera using the optoelectronic shutter 360 according to the present exemplary embodiment.

The camera using the optoelectronic shutter 360 according to the present exemplary embodiment may be used with obtaining a 3D image, recognizing a 3D environment of a robot, radar for military laser, an input device for 3D display, and 3D shape measurement using phase shifting.

In addition, the present exemplary embodiment relates the optical apparatus 300 using the optoelectronic shutter 360 and the camera as the optical apparatus 300 has been illustrated. However, for example, the optoelectronic shutter 360 may be used in mixing array input lights and in transmitting the mixed array input lights as several transmission lights in various fields of optical communication.

A method of detecting phase delay from output light by using the optoelectronic shutter 360 shown in FIG. 11 according to an exemplary embodiment will now be described with reference to FIGS. 12A, 12B, and 13. According to the present exemplary embodiment, an irradiation light such as Li of FIG. 11 has a sine waveform.

Figure 12A:
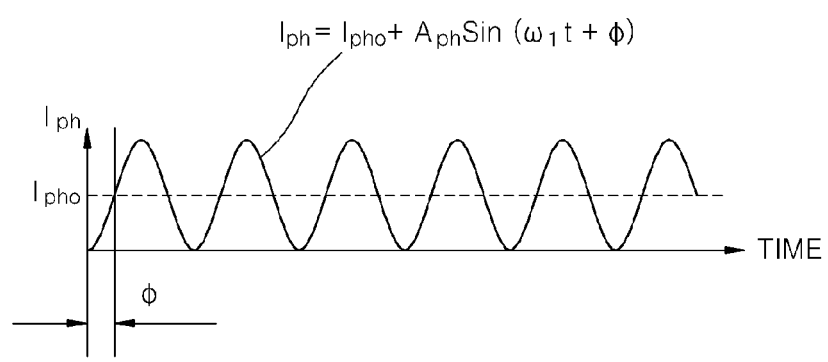
FIGS. 12A and 12B are graphs showing mixing of reflected light having a phase delay with respect to irradiated light having a sine waveform, and a signal that is modulated by an optoelectronic shutter.
Figure 12B:
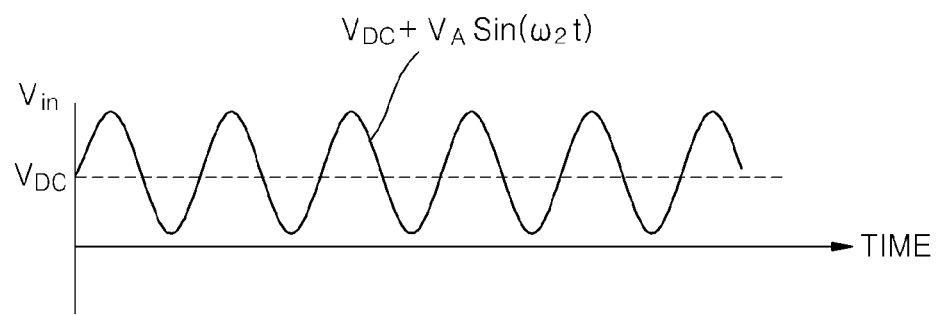

FIGS. 12A and 12B are graphs showing mixing of a reflection light having a phase delay with respect to an irradiation light having a sine waveform, and a signal that is modulated by an optoelectronic shutter such as 360 of FIG. 11.

An input light such as L1 of FIG. 11, which is input to an optoelectronic shutter such as 360 of FIG. 11, i.e., a reflection light such as Lr of FIG. 11 reflected by an object such as O of FIG. 11, has a phase delay $\phi$ with respect to the irradiation light Li. FIG. 12A illustrates a light current $I_{ph}$ generated due to the input light L1 with respect to a time axis and shows that the input light L1 is phase-delayed by a phase delay $\phi$.

FIG. 12B is a graph showing that an applied bias voltage is given as the sum of $V_{DC}$ as a DC bias voltage and a local oscillation component $V_A^* \sin \omega_2 t$. The local oscillation component $V_A^* \sin \omega_2 t$ may be used to modulate a base-emitter voltage or a base current.

Figure 13:
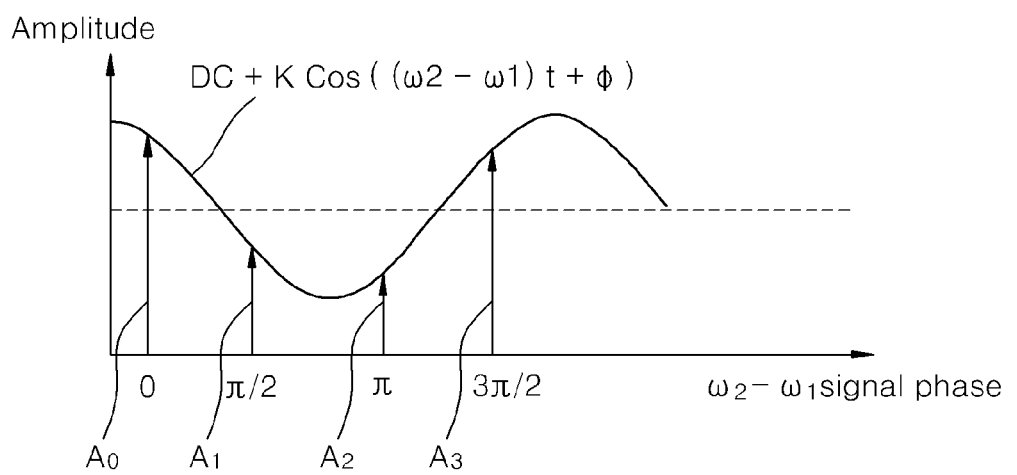
FIG. 13 is a graph showing amplitude of output light that is modulated by an optoelectronic shutter and is output, with respect to irradiated light having a sine waveform, against phase delay.

FIG. 13 is a graph showing the amplitude of an output light (L2 of FIG. 11) in which the light current $I_{ph}$ generated due to the input light L1 is mixed with a bias voltage having a local oscillation component and is output to have a phase delay $\phi$. In FIG. 13, the vertical axis represents the amplitude of the output light L2 output by a light emitting diode such as 310 of FIG. 11 of an optoelectronic shutter such as 360 of FIG. 11. As shown in Equation 4 or 9 as described above, the output signal output from an optoelectronic shutter such as 360 of FIG. 11 may be gain-modulated by using a base-emitter voltage modulation method or a base current modulation method. In this case, the gain-modulated output signal is given as a low-frequency cosine function of a beat frequency $(\omega_2-\omega_1)$ and has the phase delay $\phi$.

The phase delay $\phi$ may be obtained by sampling values of amplitudes with respect to different phases of a signal over one period three times or more, for example. The phase delay $\phi$ may be obtained by using a four-phase shift method using four-time sampling and a five-phase shift method using five-time sampling.

FIG. 13 is a graph showing a four-phase shift method. When the brightness of an image that is obtained by controlling an exposure time by trigger control of an optical image sensor is A, in the four-phase shift method, four brightnesses $A_0, A_1, A_2$, and $A_3$ of an image that correspond to phases such as $\phi+0$, $\phi+\pi/2$, $\phi+\pi$, and $\phi+3\pi/2$ are obtained from an output signal over one period. If the value of $A_i$ is small, $\Sigma Ai$ is obtained by adding the brightnesses $A_0, A_1, A_2$, and $A_3$, and the phase delay $\phi$ may be obtained by using Equation 10:

$$\phi = \tan^{-1}((A_0-A_2)/(A_1-A_3)) \tag{10}$$

In the optoelectronic shutter 360 shown in FIG. 11, an output signal that is used to drive a light emitting diode such as 310 of FIG. 11 includes a DC bias component. In the described above four-phase shift method, the phase delay $\phi$ is obtained by using a difference ratio and thus the DC component does not affect the four-phase shift method. Also, in the four-phase shift method, even though a secondary non-linear component is present in the brightness Ai of the image, the secondary non-linear component is cancelled, and the same phase delay may be obtained.

In the four-phase shift method, a camera has frame speed that is four times a frequency of an output signal output from an optoelectronic shutter. When the frequency of the output signal is 30 sec$^{-1}$ (Hz), the camera has to output images at 120 frames per second. A commercialized CCD camera may control an exposure time in units of about 1/10,000 seconds to about 1/1,000 seconds, and thus output of images may be obtained by a commercialized camera.

If the phase delay $\phi$ is obtained, a distance R may be calculated as $c/4\pi f^*\phi$. Here, c is $3\times10^5$ km/sec ($3\times10^8$ m/sec), which is the speed of light, and f is a modulation frequency of an irradiation light, i.e., $2\pi\omega_1$.

Figure 14A:
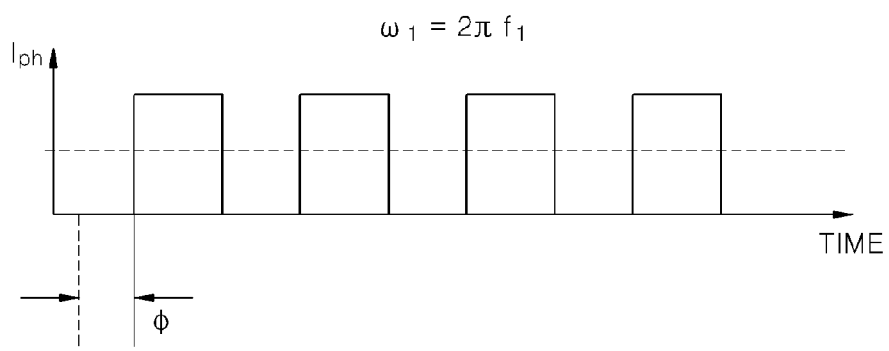
FIGS. 14A and 14B are graphs showing mixing of reflected light having a phase delay with respect to irradiated light having a rectangular waveform, and a signal that is modulated by an optoelectronic shutter.
Figure 14B:
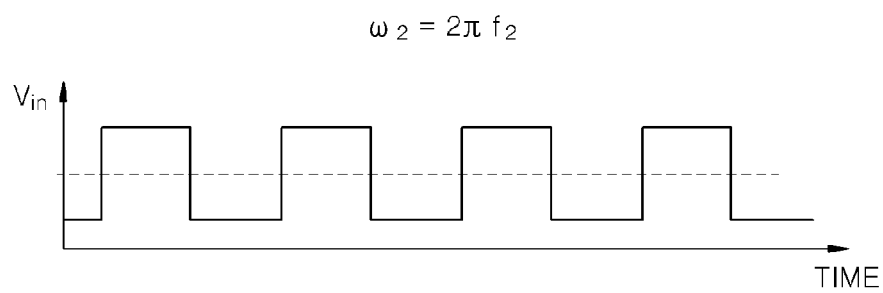
Figure 15:
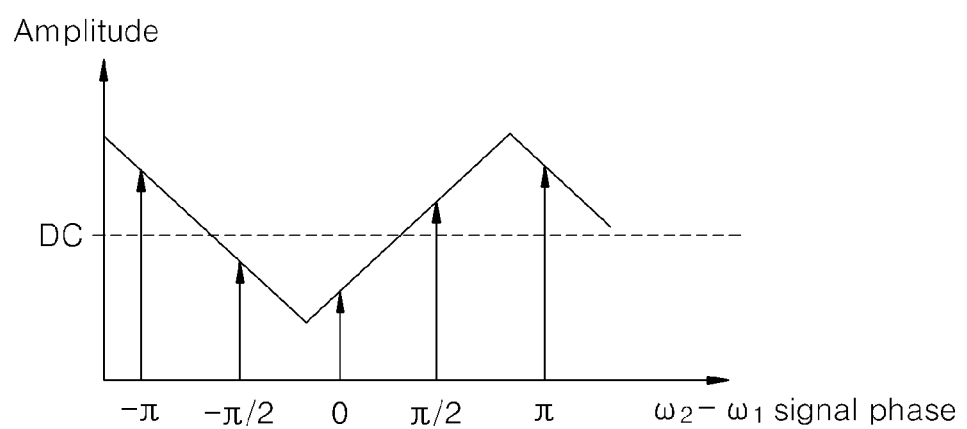
FIG. 15 is a graph showing amplitude of output light that is modulated by an optoelectronic shutter and is output, with respect to irradiated light having a rectangular waveform, against phase delay.

FIGS. 14A, 14B, and 15 illustrate a method of detecting a phase delay from an output light by using the optoelectronic shutter 360 shown in FIG. 11, according to another exemplary embodiment. The present exemplary embodiment is a case when an irradiation light such as Li of FIG. 11 has a rectangular waveform, i.e., a pulse waveform.

FIGS. 14A and 14B are graphs showing mixing of reflected light having a phase delay with respect to an irradiation light having a rectangular waveform and a signal that is modulated by an optoelectronic shutter (360 of FIG. 11).

An input light (L1 of FIG. 11) that is input to the optoelectronic shutter (360 of FIG. 11) has a phase delay $\phi$ with respect to the irradiated light Li. FIG. 14A illustrates a light current $I_{ph}$ generated due to the input light L1 with respect to a time axis and shows that the input light L1 is phase-delayed by a phase delay $\phi$.

FIG. 14B is a graph showing that an applied bias voltage has a rectangular waveform having a frequency $\omega_2$. The local oscillation component of the applied bias voltage having a rectangular waveform may be used to modulate a base-emitter voltage or a base current, as in the previous exemplary embodiment.

FIG. 15 is a graph showing amplitude of an output light (L2 of FIG. 11) in which the light current $I_{ph}$ generated due to the input light L1 is mixed with a bias voltage having a local oscillation component and is output to have the phase delay $\phi$. The output light L2 output from the optoelectronic shutter (360 of FIG. 11) and gain-modulated has a triangular-waveform amplitude due to the phase delay $\phi$ of the input light L1. Also, the output light L2 has a frequency that corresponds to a beat frequency $(\omega_2-\omega_1)$ and has the phase delay $\phi$.

When the phase delay $\phi$ is obtained by sampling, an error may occur due to a high-order frequency, and sampling is not an ideal pulse but has a given width and thus the efficiency of modulation may be lowered, and the number of sampling increases so as to reduce the error. The phase delay $\phi$ may be obtained by using a five-phase shift method, as shown in FIG. 15. In this case, the phase delay $\phi$ may be calculated from five brightnesses of an image of that correspond to phases such as ω−π, φ−π/2, φ+0, φ+π/2, and φ+π over one period of an output signal.

As described above, the optoelectronic shutter (360 of FIG. 11) modulates a current gain β at a low voltage and at a low current and converts a high-frequency input signal into a low-frequency image output, thereby measuring the phase delay φ by using a CCD camera or a CMOS camera. Thus, distances may be measured based on a time-of-flight (TOF) method by using a camera that takes 3D images.

A method of manufacturing an optoelectronic shutter according to an exemplary embodiment will now be described.

Figure 16A:
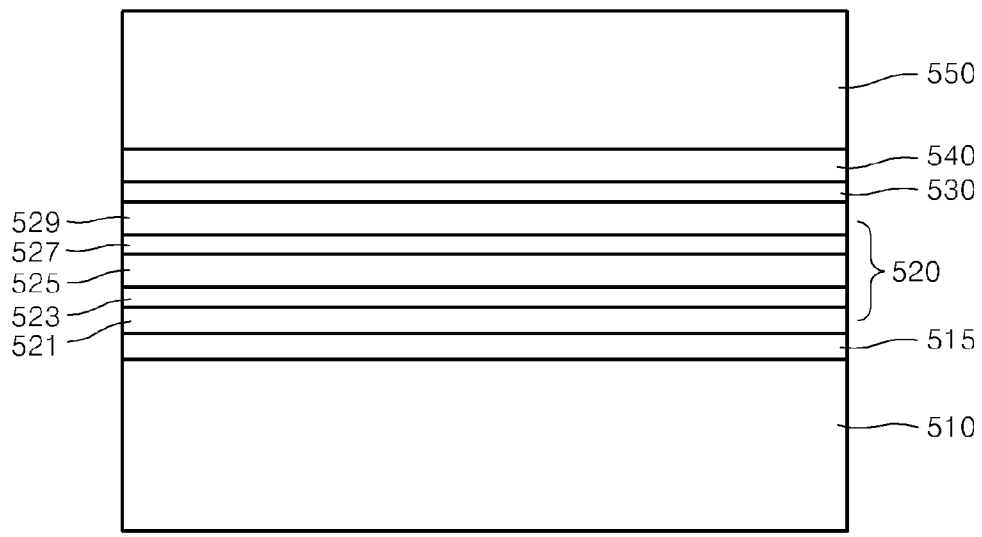
FIGS. 16A through 16G are cross-sectional views illustrating a method of manufacturing an optoelectronic shutter, according to an exemplary embodiment.

FIGS. 16A through 16G are cross-sectional views illustrating a method of manufacturing an optoelectronic shutter, according to an exemplary embodiment. Referring to FIG. 16A, a sacrificial layer 515, an NPN transistor layer 520, a reflection layer 530, a tunnel junction layer 540, and a light emitting diode layer 550 are sequentially stacked on a substrate 510. The substrate 510 may be a GaAs substrate, for example. The sacrificial layer 515 may be formed of AsGaAs, AlAs or InGaP, for example, to have a thickness of about 10 nm. The sacrificial layer 515 is disposed so as to perform a lift-off process that will be described later.

First, a sub-collector layer 521, a collector layer 523, a base layer 525, an emitter layer 527, and a sub-emitter layer 529 are sequentially stacked on the sacrificial layer 515, thereby forming the NPN transistor layer 520. The doping concentration of the base layer 525 is related to the optical gain of a phototransistor such as 230 of FIG. 8 and the electrical characteristic of first and second transistors such as 270 and 281 of FIG. 8 and thus is set to be uniform. For example, the base layer 525 is formed of P-type GaAs to have a doping concentration of $4 \times 10^{18}/cm^3$. Next, the reflection layer 530 and the tunnel junction layer 540 are formed, and then the light emitting diode 550 layer is formed. An example of an epitaxial layer including the NPN transistor layer 520 and the light emitting diode layer 550 is shown in Table 1.

Figure 16B:
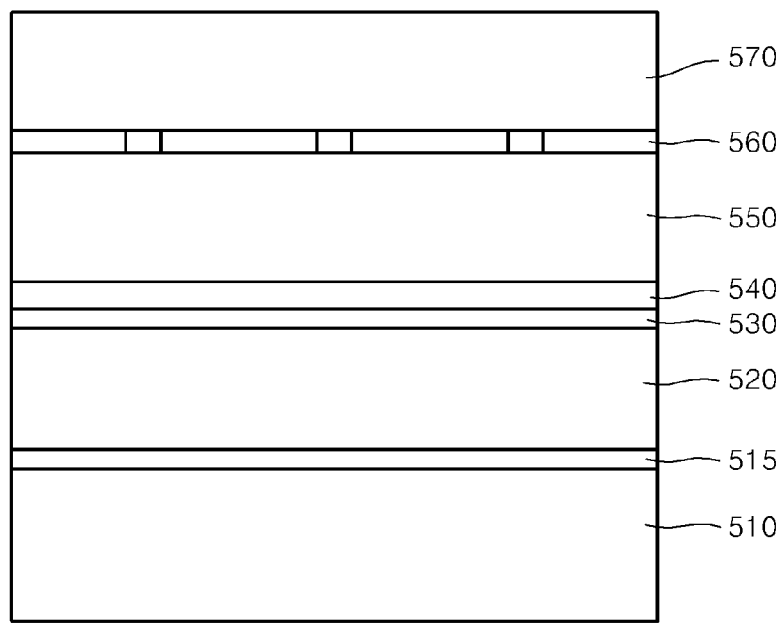
Figure 16C:
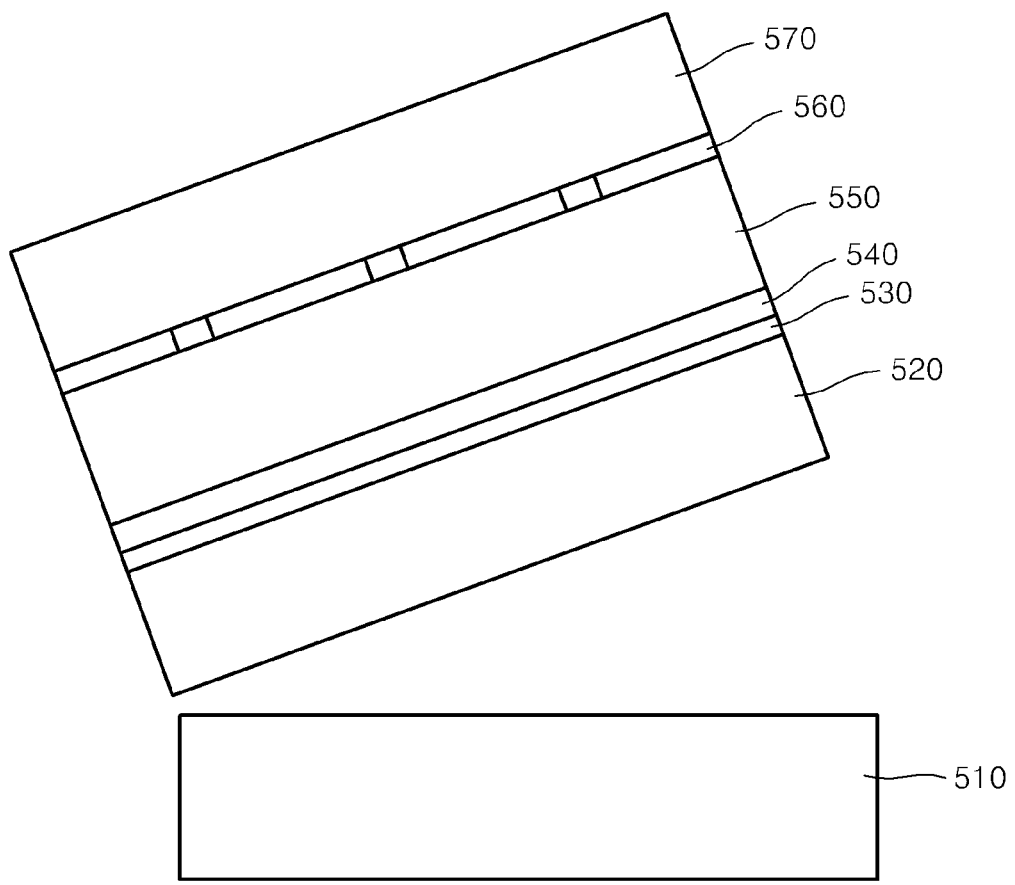

Referring to FIG. 16B, a lower electrode layer 560 is formed on the light emitting diode layer 550, and a transparent substrate 570 is joined to a surface on which the lower electrode layer 560 is disposed. The transparent substrate 570 may be a glass substrate or a sapphire substrate. Referring to FIG. 16C, the substrate 510 is removed by performing a lift-off process. In this case, a sacrificial layer (515 of FIG. 16A) is removed, thereby removing the substrate 510 from the rest of the stack structure.

Figure 16D:
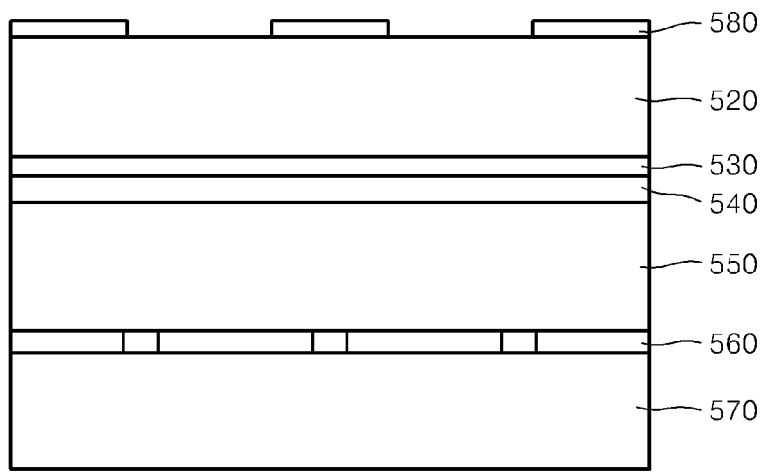
Figure 16E:
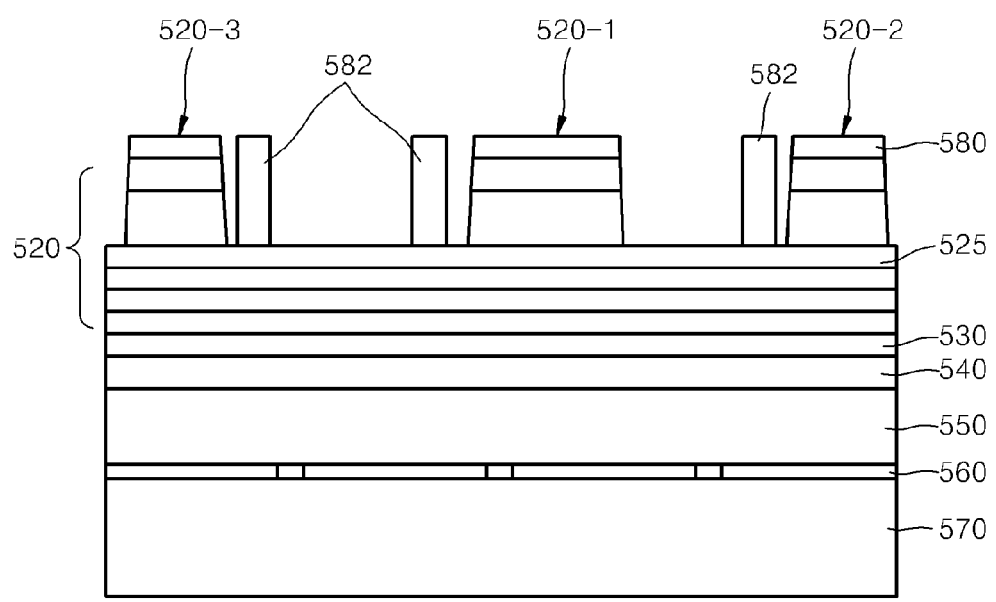

Referring to FIG. 16D, a collector electrode layer 580 of the transistor layer 520 is formed. Referring to FIG. 16E, a phototransistor region 520-1 and first and second transistor regions 520-2 and 520-3 are separated from one another by performing an etching process. In this case, the etching process is performed so that the base layer 525 of the transistor layer 520 may be exposed, and base electrodes 582 that correspond to the phototransistor region 520-1 and the first and second transistor regions 520-2 and 520-3, respectively, are formed. The phototransistor region 520-1 and the first and second transistor regions 520-2 and 520-3 may also be formed in a mesa structure by performing mesa etching.

Figure 16F:
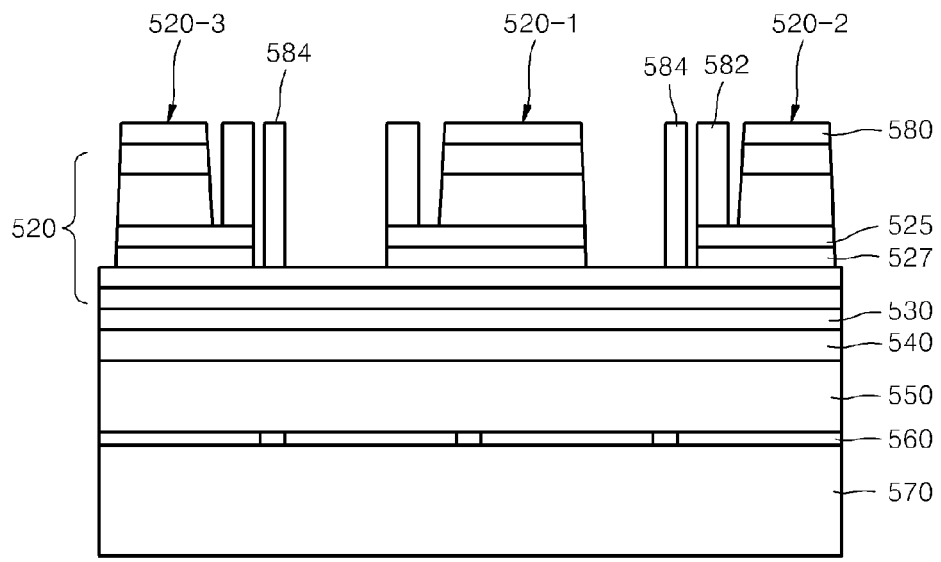

Referring to FIG. 16F, an etching process is performed so that part of the emitter layer 527 of the transistor layer 520 may be exposed, and emitter electrodes 584 that correspond to the first and second transistor regions 520-2 and 520-3, respectively, are disposed on the exposed emitter layer 527.

Figure 16G:
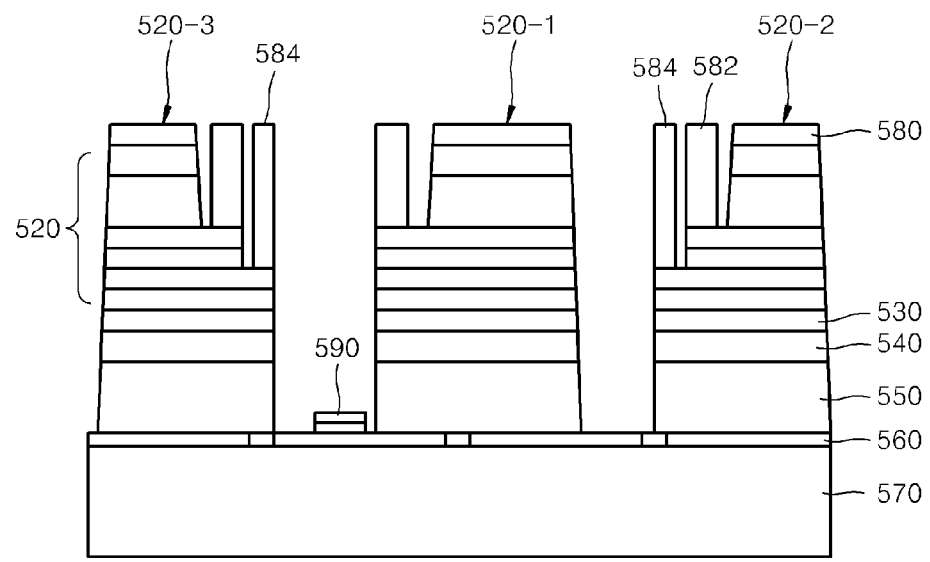

Referring to FIG. 16G, trenches are formed between the phototransistor region 520-1 and the first and second transistor regions 520-2 and 520-3. In this case, an etching process may be performed so that the phototransistor region 520-1 and the first and second transistor regions 520-2 and 520-3 are separated from one another into a plurality of unit pixels P, as illustrated in FIG. 4 or 9. Next, a metal-insulator-metal (MIM) capacitor 590 is disposed adjacent to the phototransistor region 520-1, and a wiring process is performed. Next, an insulating layer (not shown) is disposed so as to cover the phototransistor region 520-1, the first and second transistor regions 520-2 and 520-3, and the capacitor 590, a planariza-

TABLE 1

| Layer | | Material | Thickness (nm) | Doping concentration (/cm³) |
|---|---|---|---|---|
| Light emitting diode layer | Cathode | N+ GaP | 2,000 | $1 \times 10^{18}$ |
| | Cladding | N, GaP | 500 | $4 \times 10^{17}$ |
| | Visible LED (MQW) | InGaP/AlGaInP | 700 | undoped |
| | Cladding | P+ GaP | 500 | $5 \times 10^{18}$ |
| Tunnel junction layer | Tunnel junction | P++ GaAs | 20 | $>1 \times 10^{19}$ |
| | | N++ GaAs | 20 | $>1 \times 10^{19}$ |
| Reflection layer | DBR | N+ $Al_{0.3}Ga_{0.7}As$ | 200 | $8 \times 10^{18}$ |
| | | N+ GaAs | 200 | $8 \times 10^{18}$ |
| Transistor layer | Sub-emitter | N+ GaAs | 50 | $5 \times 10^{18}$ |
| | Emitter | N, InGaP | 100 | $5 \times 10^{17}$ |
| | Base | P, GaAs | 80 | $4 \times 10^{18}$ |
| | Collector | N−, GaAs or InGaAs | 800 | $1 \times 10^{16}$ |
| | Sub-collector | N+, GaAs, or InGaP, or AlGaAs | 600 | $5 \times 10^{18}$ |
| | Sacrificial layer | AlGaAs, AlAs or InGaP | 10 | $5 \times 10^{18}$ |
| Substrate | Substrate | GaAs | 350000 | S.I. |

The thicknesses and doping concentrations of the transistor layer 520, the reflection layer 530, the tunnel junction layer 540, and the light emitting diode layer 550 of the epitaxial layer are shown in Table 1. The epitaxial layer may be formed by using an epitaxial growth method using a metal organic chemical vapor deposition (MOCVD) or a molecular beam epitaxy (MBE) process.

tion process is performed on a top surface of the insulating layer, and an anti-reflection (AR) coating layer may be disposed on the planarized insulating layer. Next, via holes are formed in the insulating layer, and a wiring process is performed, thereby manufacturing an optoelectronic shutter 200 such as 210 of FIG. 8.

As described above, in the optoelectronic shutter according to the one or more of the above exemplary embodiments of the present invention may be small-sized, and an image may be directly formed on a semiconductor substrate and thus costs may be reduced.

The lift-off process is used in the present exemplary embodiment. However, for example, a process of forming upper electrodes may be performed without performing a process of removing a substrate such as 510 of FIG. 16C in the method of manufacturing the optoelectronic shutter described above.

The method of manufacturing the optoelectronic shutter according to the present exemplary embodiment has been described based on the structure of the optoelectronic shutter described with reference to FIG. 8. The structure of the optoelectronic shutter 100 described with reference to FIG. 3 may be interpreted as a simplified structure of the optoelectronic shutter 200 described with reference to FIG. 8. Thus, a description of a method of manufacturing an optoelectronic shutter with reference to FIG. 3 will not be repeated.

In the one or more of the above exemplary embodiments of the present invention, the input light L1 is infrared light having a wavelength of about 800 nm, and the output light L2 is red light having a wavelength of about 600 nm to about 700 nm. However, the wavelength of the input light L1 and the wavelength of the output light L2 may be properly selected according to an optical apparatus including the optoelectronic shutter.

As described above, in an optoelectronic shutter, the method of operating the same, and the optical apparatus including the optoelectronic shutter according to the one or more of the above exemplary embodiments of the present invention, first, the optoelectronic shutter modulates the current gain of a phototransistor to modulate output light with respect to input light and thus may be driven at a low voltage and at a low current. Second, the optoelectronic shutter may output low-frequency output light with respect to high-frequency input light and thus may detect a phase delay by using a general CCD image sensor or a general CMOS image sensor. Also, the phase delay may be detected so that a distance may be measured based on a time-of-flight (TOF) method and thus the optoelectronic shutter may be applied to a camera that takes 3D images. Third, the optoelectronic shutter is highly integrated and thus may have improved resolution so that an image of a distant object having high resolution may be obtained. Fourth, the optoelectronic shutter may be manufactured by performing a general semiconductor manufacturing process and thus may be manufactured with low costs.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An optoelectronic shutter comprising:
    a phototransistor which generates an output signal from incident input light;
    a light emitting diode serially connected to the phototransistor, and
    a capacitor disposed in parallel to the light emitting diode wherein the light emitting diode outputs output light according to the output signal,
    wherein the output signal is gain-modulated according to a modulation of a current gain of the phototransistor,
    wherein the light emitting diode and the phototransistor are stacked on a substrate in a vertical direction.

2. The optoelectronic shutter of claim 1, wherein the phototransistor is a heterojunction phototransistor having a triode structure.

3. The optoelectronic shutter of claim 1, wherein the light emitting diode comprises a P-type cladding layer, an active layer, and an N-type cladding layer that are sequentially stacked on the substrate, and the phototransistor comprises a collector layer, a base layer, and an emitter layer that are stacked sequentially on the light emitting diode.

4. The optoelectronic shutter of claim 3, wherein a direct current (DC) voltage supply source, which applies a DC bias voltage, is connected to a base of the phototransistor, and an alternating current (AC) voltage supply source, which applies an AC voltage for local oscillation of a base-emitter voltage, is connected to an emitter of the phototransistor, and a forward voltage is applied to the P-type cladding layer of the light emitting diode.

5. The optoelectronic shutter of claim 3, wherein an emitter electrode disposed on an upper portion of the emitter layer comprises a transparent conductive material, and the input light is incident on the emitter electrode.

6. The optoelectronic shutter of claim 5, wherein an anti-reflection (AR) layer is disposed on the emitter electrode.

7. The optoelectronic shutter of claim 3, wherein the optoelectronic shutter has a structure in which a plurality of unit pixels are arranged, and one of a plurality of phototransistors and one of a plurality of light emitting diodes constitute one of the unit pixels.

8. The optoelectronic shutter of claim 7, wherein a forward voltage is commonly applied to the P-type cladding layer of the light emitting diode of each of the plurality of unit pixels, a DC bias voltage is applied to a base of the phototransistor of each of the unit pixels, and an AC bias voltage for local oscillation of a base-emitter voltage is commonly applied to an emitter of the phototransistor of each of the unit pixels.

9. The optoelectronic shutter of claim 1, wherein the light emitting diode comprises an N-type cladding layer, an active layer, and a P-type cladding layer that are sequentially stacked on the substrate, and the phototransistor comprises an emitter layer, a base layer, and a collector layer that are stacked sequentially on the light emitting diode.

10. The optoelectronic shutter of claim 9, wherein a base current modulation unit is connected to a base of the phototransistor.

11. The optoelectronic shutter of claim 10, wherein the base current modulation unit comprises:
    a first transistor which generates a current signal that is used to modulate the base current; and
    a current source which generates a bias current that flows through the base of the phototransistor according to the current signal generated by the first transistor.

12. The optoelectronic shutter of claim 11, wherein an AC voltage for local oscillation of the base current is applied to a base of the first transistor, a collector of the first transistor is connected to a collector of the phototransistor, and an emitter of the first transistor is connected to the base of the phototransistor.

13. The optoelectronic shutter of claim 12, wherein the current source is a second transistor, a collector and a base of the second transistor are connected to the emitter of the first transistor, and an emitter of the second transistor is connected to ground or a negative voltage supply source.

14. The optoelectronic shutter of claim 13, wherein the first and second transistors are heterojunction bipolar transistors.

15. The optoelectronic shutter of claim 12, wherein:
    the optoelectronic shutter comprises a structure in which a plurality of pixels are arranged, and one of a plurality of phototransistors, one of a plurality of first transistors, one of a plurality of current sources, and one of a plurality of light emitting diodes constitute one of the unit pixels.

16. The optoelectronic shutter of claim 15, wherein a ground voltage or a negative voltage is commonly applied to the N-type cladding layer of the light emitting diode of each of the plurality of unit pixels, a bias voltage is commonly applied to the collector of the phototransistor of each of the unit pixels, and an AC bias voltage for local oscillation of a base current is commonly applied to a base of the first transistor of each of the unit pixels.

17. The optoelectronic shutter of claim 9, wherein a tunnel junction layer is interposed between the light emitting diode and the phototransistor.

18. The optoelectronic shutter of claim 9, wherein a collector electrode disposed on an upper portion of the collector layer comprises a transparent conductive material, and the input light is incident on the collector electrode.

19. The optoelectronic shutter of claim 1, wherein a reflection layer which reflects an output light emitted from the light emitting diode is interposed between the light emitting diode and the phototransistor.

20. The optoelectronic shutter of claim 19, wherein the reflection layer is a distributed Bragg reflector (DBR) layer.

21. The optoelectronic shutter of claim 1, wherein the substrate comprises glass, sapphire, or GaAs.

22. The optoelectronic shutter of claim 1, wherein the light emitting diode is a GaP-based red light emitting diode.

23. A method of operating an optoelectronic shutter including a phototransistor which generates an output signal from incident input light and a light emitting diode serially connected to the phototransistor, wherein the light emitting diode outputs output light according to the output signal, and the output signal is gain-modulated according to a modulation of a current gain of the phototransistor, the method comprising:
modulating a base-emitter voltage of the phototransistor to modulate a current gain of the phototransistor,
wherein a DC bias voltage is applied to a base of the phototransistor, and an AC voltage for local oscillation of the base-emitter voltage is applied to an emitter of the phototransistor.

24. The method of claim 23, wherein a modulation frequency of the base-emitter voltage is different from a modulation frequency of the input light.

* * * * *